US012791564B2

(12) United States Patent
Mrksich et al.

(10) Patent No.: US 12,791,564 B2
(45) Date of Patent: Nov. 10, 2026

(54) TRACELESS IMMOBILIZATION OF ANALYTES FOR SAMDI MASS SPECTROMETRY

(71) Applicant: NORTHWESTERN UNIVERSITY, Evanston, IL (US)

(72) Inventors: Milan Mrksich, Hinsdale, IL (US); Kazi Y. Helal, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 790 days.

(21) Appl. No.: 16/972,386

(22) PCT Filed: Jun. 7, 2019

(86) PCT No.: PCT/US2019/036081
§ 371 (c)(1),
(2) Date: Dec. 4, 2020

(87) PCT Pub. No.: WO2019/237019
PCT Pub. Date: Dec. 12, 2019

(65) Prior Publication Data
US 2021/0231677 A1 Jul. 29, 2021

Related U.S. Application Data

(60) Provisional application No. 62/682,153, filed on Jun. 7, 2018.

(51) Int. Cl.
*G01N 33/68* (2006.01)
*C12Q 1/26* (2006.01)

(52) U.S. Cl.
CPC .......... *G01N 33/6851* (2013.01); *C12Q 1/26* (2013.01); *G01N 2610/00* (2013.01)

(58) Field of Classification Search
CPC .......... G01N 33/6851; G01N 2610/00; G01N 33/543; G01N 33/6848; C12Q 1/26; C12Q 1/00
See application file for complete search history.

(56) References Cited

U.S. PATENT DOCUMENTS 6,288,390 B1 9/2001 Siuzdak et al.
7,445,885 B2 11/2008 Heinzle et al.
(Continued)

FOREIGN PATENT DOCUMENTS

WO WO-2016/138015 A1 9/2016
WO WO-2017/214151 A1 12/2017
(Continued)

OTHER PUBLICATIONS

Anderson et al., Measuring Drug Metabolism Kinetics and Drug-Drug Interactions Using Self-Assembled Monolayers for Matrix-Assisted Laser Desorption-Ionization Mass Spectrometry, Anal. Chem., 88(17):8604-9 (Sep. 2016).
(Continued)

*Primary Examiner* — Samuel P Siefke
(74) *Attorney, Agent, or Firm* — MARSHALL, GERSTEIN & BORUN LLP

(57) ABSTRACT

The present disclosure is directed to materials and methods of high throughput, traceless immobilization of analytes for use in self-assembled monolayer for matrix-assisted laser desorption and ionization (SAMDI) mass spectrometry. Methods of the disclosure are useful, in various embodiments, for measuring the activity of an enzyme or for monitoring a chemical reaction.

18 Claims, 8 Drawing Sheets

(56) References Cited

U.S. PATENT DOCUMENTS

| | | | |
|---|---|---|---|
| 8,580,571 B2 | 11/2013 | Nishimi et al. | |
| 9,046,527 B2 | 6/2015 | Galisson et al. | |
| 9,234,848 B2 | 1/2016 | Pecheur et al. | |
| 11,047,861 B2 | 6/2021 | Mrksich et al. | |
| 2007/0213278 A1 | 9/2007 | Wong et al. | |
| 2007/0266775 A1* | 11/2007 | Nishimi | G01N 33/54393 204/403.01 |
| 2008/0070324 A1 | 3/2008 | Floyd | |
| 2008/0128608 A1 | 6/2008 | Northen et al. | |
| 2009/0163380 A1 | 6/2009 | Stolowitz et al. | |
| 2010/0011456 A1 | 1/2010 | Marthur et al. | |
| 2010/0112722 A1 | 5/2010 | Mrksich et al. | |
| 2014/0134642 A1 | 5/2014 | Mrksich et al. | |
| 2014/0206570 A1 | 7/2014 | Mrksich et al. | |
| 2015/0136972 A1 | 5/2015 | Lasch et al. | |
| 2016/0252501 A1 | 9/2016 | Mrksich et al. | |
| 2017/0059576 A1 | 3/2017 | Famulok et al. | |
| 2018/0080058 A1 | 3/2018 | Mrksich et al. | |

FOREIGN PATENT DOCUMENTS

| | | |
|---|---|---|
| WO | WO-2019/168980 A1 | 9/2019 |
| WO | WO-2019/200262 A1 | 10/2019 |
| WO | WO-2019/237019 A1 | 12/2019 |

OTHER PUBLICATIONS

Arabaci et al., "α-Haloacetophenone Derovatoves as photoreversible Covalent Inhibitors of Protein Tyrosine Phosphatases," J. Am. Chem. Soc 121, (21), 5085-5086 (1999).

Ban et al., Discovery of glycosyltransferases using carbohydrate arrays and mass spectrometry, Nat. Chem. Biol., 8(9):769-73 (Sep. 2012).

Ban et al., On-chip synthesis and label-free assays of oligosaccharide arrays, Angew. Chem. Int. Ed. Engl., 47(18):3396-9 (2008).

Bellis S., Advantages of RGD peptides for directing cell association with biomaterials, Biomaterials, vol. 32, Iss. 18, 4205-4210 (Jun. 2011).

Bernard et al., "Staurosporine-induced apoptosis of HPV positive and negative human cervical cancer cells from different points in the cell cycle," Cell Death Differ 8: 234-244 (2001).

Berns et al., "Cellular Assays with a Molecular Endpoint Measured by SAMDI Mass Spectrometry," Small 12(28):3811-3818 (2016).

Cai et al., Enzymatic synthesis and properties of uridine-5'-O-(2-thiodiphospho)-N-acetylglucosamine. *Carbohydr. Res.* 346: 1576-80 (2011).

De Rond et al., High throughput screening of enzyme activity with mass spectrometry imaging, Curr. Opin. Biotechnol., 31:1-9 (Feb. 2015).

Deshmukh et al., "A regenerative approach to the treatment of multiple sclerosis," Nature, 502:327-332 (2013).

Diagne et al., SAMDI Mass Spectrometry-Enabled High-Throughput Optimization of a Traceless Petasis Reaction, ACS Comb. Sci., 17(11):658-62 (Nov. 2015).

Dillmore et al., A photochemical method for patterning the immobilization of ligands and cells to self-assembled monolayers. *Langmuir*, 20: 7223-31 (2004).

Ding et al., "A role for chemistry in stem cell biology," Nat. Biotechnol, 22:833-840 (2004).

Feng et al., The synergy peptide PHSRN and the adhesion peptide RGD mediate cell adhesion through a common mechanism. *Biochemistry*, 43: 15811-21 (2004).

Fox et al., "High-throughput screening: update on practices and success," J. Biomol. Screen., 11:864-869 (2006).

Gawalt et al., A substituent effects study reveals the kinetic pathway for an interfacial reaction. *J. Am. Chem. Soc.* 126: 15613-7 (2004).

Giepmans et al., "The fluorescent toolbox for assessing protein location and function," Science, 312:217-224 (2006).

Gurard-Levin et al., Combining mass spectrometry and peptide arrays to profile the specificities of histone deacetylases. *Chembiochem*. 10: 2159-61 (2009).

Gurard-Levin et al., Combining self-assembled monolayers and mass spectrometry for applications in biochips. *Annu. Rev. Anal. Chem.* (*Palo Alto Calif.*) 1: 767-800 (2008).

Gurard-Levin et al., High-throughput screening of small molecule libraries using SAMDI mass spectrometry, ACS Comb. Sci., 13(4):347-50 (Jul. 2011).

Gurard-Levin et al., Peptide arrays identify isoform-selective substrates for profiling endogenous lysine deacetylase activity, ACS Chem. Biol., 5(9):863-73 (Sep. 2010).

Gurard-Levin et al., The activity of HDAC8 depends on local and distal sequences of its peptide substrates. *Biochemistry*, 47: 6242-50 (2008).

Helal et al., Traceless Immobilization of Analytes for High-Throughput Experiments with SAMDI Mass Spectrometry, J. Am. Chem. Soc., 140(26):8060-3 (Jul. 2018).

Hellmuth et al., "Specific inhibitors of the protein tyrosine phosphatase Shp2 identified by high-throughput docking," Proc Natl Acad Sci U S A 105:7275-7280 (2008).

Hodneland et al., Design of self-assembled monolayers that release attached groups using applied electrical potentials. *Langmuir*, 13: 6001-3 (1997).

Hodneland et al., Selective immobilization of proteins to self-assembled monolayers presenting active site-directed capture ligands. *Proc. Natl. Acad. Sci. USA*, 99: 5048-52 (2002).

Hooff et al., "Characterization of Beta-Lactamase Enzyme Activity in Bacterial Lysates using MALDI-Mass Spectrometry," J. Proteome Res., 11:79-84 (2012).

Houseman et al., Carbohydrate arrays for the evaluation of protein binding and enzymatic modification. *Chem. Biol.* 9: 443-54 (2002).

Houseman et al., Environment of Arg-Gly-Asp ligands influences the adhesion of fibroblasts to self-assembled monolayers. *Cell Attachment to the Extracellular Matrix*, p. 430a, Abstract 2494 (1998).

Houseman et al., Maleimide-Functionalized Self-Assembled Monolayers for the Preparation of Peptide and Carbohydrate Biochips, 19(5):1522-31 (2003).

Houseman et al., Model substrates for the dynamic control of cell behavior. *Extracellular Matrix Cell Bahavior*, p. 45a, Abstract 232 (2000).

Houseman et al., Model systems for studying polyvalent carbohydrate binding interactions. *Top. Curr. Chem.* 218: 1-44 (2002).

Houseman et al., Peptide chips for the quantitative evaluation of protein kinase activity. *Nat. Biotechnol.* 20: 270-4 (2002).

Houseman et al., The microenvironment of immobilized Arg-Gly-Asp peptides is an important determinant of cell adhesion. *Biomaterials*, 22: 943-55 (2001).

Houseman et al., The role of ligand density in the enzymatic glycosylation of carbohydrates presented on self-assembled monolayers of alkanethiolates on gold. *Angew. Chem. Int. Ed.* 38: 782-5 (1999).

Houseman et al., Towards quantitative assays with peptide chips: a surface engineering approach. *Trends Biotechnol.* 20: 279-81 (2002).

Houseman et al., Using self-assembled monolayers that present Arg-Gly-Asp peptide ligands to study adhesion of fibroblasts. *Extracellular Matrix-Cell Interaction*, 11: p. A1095, Abstract 1395 (1997).

Huang et al., Photooxidation of thiols in self-assembled monolayers on gold, J. Am. Chem. Soc., 115(8):3342-3 (1993).

Inglese et al., "High-throughput screening assays for the identification of chemical probes," Nat. Chem. Biol. 3(8):466-479 (2007).

International Application No. PCT/US2019/036081, International Search Report and Written Opinion, mailed Nov. 20, 2019.

International Preliminary Report on Patentability for Application No. PCT/US2016/046027, dated Feb. 13, 2018.

International Search Report and Written Opinion for Application No. PCT/US2016/046027, dated Oct. 31, 2016.

Johnson et al., "A stem cell-based approach to cartilage repair," Science, 336:717-721 (2012).

(56) References Cited

OTHER PUBLICATIONS

Kanoh et al., Immobilization of natural products on glass slides by using a photoaffinity reaction and the detection of protein-small-molecule interactions, Angew Chem Int Ed Engl., 42(45):5584-7 (Nov. 2003).
Kanoh et al., Photo-cross-linked small-molecule microarrays as chemical genomic tools for dissecting protein-ligand interactions, Chem. Asian J., 1(6):789-97 (Dec. 2006).
Kanoh et al., SPR imaging of photo-cross-linked small-molecule arrays on gold, Anal. Chem., 78(7):2226-30 (Apr. 2006).
Kato et al., "Using Model Substrates to Study the Dependence of Focal Adhesion Formation on the Affinity of Integrin-Ligand Complexes," Biochemistry 43:2699-2707 (2004).
Kato et al., 7. Using model substrates to study the influence of affinity on cell adhesion. Abstracts, Division of Biological Chemistry, 222nd National Meeting of the American Chemical Society, Aug. 26-29, 2001, *Biochemistry*, 40: 8607-64 (2001).
Kato et al., Rewiring cell adhesion. *J. Am. Chem. Soc.* 126: 6504-5 (2004).
Kilian et al., "Directing stem cell fate by controlling the affinity and density of ligand-receptor interactions at the biomaterials interface," Angew Chem Int Ed Engl. 51(20):4891-5 (2012).
Kim et al., Profiling the selectivity of DNA ligases in an array format with mass spectrometry. *Nucleic Acids Res.* 38: e2 (2010).
Krska et al., The Evolution of Chemical High-Throughput Experimentation To Address Challenging Problems in Pharmaceutical Synthesis, Acc. Chem. Res., 50(12):2976-85 (Dec. 2017).
Kuo et al., Profiling deacetylase activities in cell lysates with peptide arrays and SAMDI mass spectrometry, Anal. Chem., 85(22):10635-42 (Nov. 2013).
Kwon et al., Dependence of the rate of an interfacial Diels-Alder reaction on the steric environment of the immobilized dienophile: an example of enthalpy-entropy compensation. *J. Am. Chem. Soc.* 124: 806-12 (2002).
Lang et al., "Cellular imaging in drug discovery," Nat. Rev. Drug Discov., 5:343-356 (2006).
Lee et al., Protein nanoarrays generated by dip-pen nanolithography. *Science*, 295: 1702-5 (2002).
Li et al., Catalytic asymmetric dihydroxylation by gold colloids functionalized with self-assembled monolayers. *Langmuir*, 15: 4957-9 (1999).
Li et al., Rapid evaluation and screening of interfacial reactions on self-assembled monolayers. *Langmuir*, 23: 11826-35 (2007).
Li et al., Steady-state of an enzymatic reaction is dependent on the density of reactant. *Langmuir*, 29: 294-8 (2013).
Liao et al., A spatially propagating biochemical reaction. *Angew. Chem. Int. Ed. Engl.* 50: 706-8 (2011).
Liao et al., An adaptor domain-mediated autocatalytic interfacial kinase reaction. *Chemistry*, 15: 12303-09 (2009).
Liu et al., In situ-generated nano-palladium-catalyzed ligand-free Suzuki-Miyaura reaction of potassium aryltrifluoroborates at room temperature, 71(23):3954-9 (Jun. 2015).
Luk et al., Self-assembled monolayers of alkanethiolates presenting mannitol groups are inert to protein adsorption and cell attachment. *Langmuir*, 16: 9604-8 (2000).
Macarron et al., "Impact of high-throughput screening in biomedical research," Nat. Rev. Drug Discov., 10:188-195 (2011).
Maduram et al., Subcellular curvature at the perimeter of micropatterned cells influences lamellipodial distribution and cell polarity. *Cell Motil. Cytoskeleton*. 65: 841-52 (2008).
Marin et al., Functional assays of membrane-bound proteins with SAMDI-TOF mass spectrometry. *Angew. Chem. Int. Ed. Engl.* 46: 8796-8 (2007).
Min et al., A method for connecting solution-phase enzyme activity assays with immobilized format analysis by mass spectrometry. *Anal. Chem.* 76: 3923-9 (2004).
Min et al., Chemical screening by mass spectrometry to identify inhibitors of anthrax lethal factor, Nat. Biotechnol., 22(6):717-23 (Jun. 2004).
Min et al., Peptide arrays: towards routine implementation. *Curr. Opin. Chem. Biol.* 8: 554-8 (2004).
Min et al., Profiling kinase activities by using a peptide chip and mass spectrometry, Angew. Chem. Int. Ed. Engl., 43(44):5973-7 (Nov. 2004).
Montavon et al., Three-component reaction discovery enabled by mass spectrometry of self-assembled monolayers, Nat. Chem., 4(1):45-51 (Dec. 2011).
Moore et al., "The Development of βLactamase as a Highly Versatile Genetic Reporter for Eukaryotic Cells," Anal. Biochem., 247:203-209 (1997).
Mrksich et al., Using self-assembled monolayers that present oligo(ethylene glycol) groups to control the interactions of proteins with surfaces. *ACS Symp. Ser.* 680: 361-73 (1997).
Mrksich et al., Using self-assembled monolayers to understand the interactions of man-made surfaces with proteins and cells. *Annu. Rev. Biophys. Biomol. Struct.* 25: 55-78 (1996).
Mrksich M., A surface chemistry approach to studying cell adhesion. *Chem. Soc. Rev.* 29: 267-73 (2000).
Mrksich M., Dynamic substrates for cell biology. *MRS Bull.* 30: 180-4 (2005).
Mrksich M., Mass spectrometry of self-assembled monolayers: a new tool for molecular surface science. *ACS Nano*, 2: 7-18 (2008).
Mrksich M., Tailored substrates for studies of attached cell culture. *Cell Mol. Life Sci.* 54: 653-62 (1998).
Mrksich M., Using self-assembled monolayers to understand the biomaterials interface. *Curr. Opin. Colloid Int. Sci.* 2: 83-8 (1997).
Mrksich M., What can surface chemistry do for cell biology? *Curr. Opin. Chem. Biol.* 6: 794-7 (2002).
Murphy et al., Substrates for cell adhesion prepared via active site-directed immobilization of a protein domain. *Langmuir*, 20: 1026-30 (2004).
Mwakwari et al., Non-peptide macrocyclic histone deacetylase inhibitors derived from tricyclic ketolide skeleton. *J. Med. Chem.* 53: 6100-11 (2010).
O'Rourke et al., "Protein localization studies in the age of 'Omics," Curr. Opin. Chem. Biol., 9(1):82-87 (2005).
Ogu et al., Drug interactions due to cytochrome P450, Proc. (Bayl Univ Med. Cent.), 13(4):421-3 (Oct. 2000).
Patel et al., "Discovery of SIRT3 Inhibitors Using SAMDI Mass Spectrometry," J. Biomol. Screen 20(7):842-848 (2015).
Patil et al., 3-Hydroxypyridin-2-thione as novel zinc binding group for selective histone deacetylase inhibition. *J. Med. Chem.* 56: 3492-506 (2013).
Patrie et al., Measurement of blood protease kinetic parameters with self-assembled monolayer ligand binding assays and label-free MALDI-TOF MS, Anal. Chem., 85(21):10597-604 (Nov. 2013).
Patrie et al., Self-assembled monolayers for MALDI-TOF mass spectrometry for immunoassays of human protein antigens. *Anal. Chem.* 79: 5878-87 (2007).
Perlman et al., "Multidimensional drug profiling by automated microscop," Science, 306:1194-1198 (2004).
Prats-Alfonso et al., Cancer prognostics by direct detection of p53-antibodies on gold surfaces by impedance measurements. *Small*, 8: 2106-15 (2012).
Roberts et al., "Using Mixed Self-Assembled Monolayers Presenting RGD and (EG)3OH Groups To Characterize Long-Term Attachment of Bovine Capillary Endothelial Cells to Surfaces," Journal of the American Chemical Society 120:6548-6555 (1998).
Roth et al., Charge derivatization of peptides for analysis by mass spectrometry, Mass Spectrom. Rev., 17(4):255-74 (Jul.-Aug. 1998).
Ruoslahti et al., "RGD and Other Recognition Sequences for Integrins," Annu. Rev. Cell Dev. Biol. 12:697-715 (1996).
Selekman et al., High-Throughput Automation in Chemical Process Development, Annu. Rev. Chem. Biomol. Eng., 8:525-47 (Jun. 2017).
Shevlin, Practical High-Throughput Experimentation for Chemists, ACS Med. Chem. Lett., 8(6):601-607 (May 2017).
Su et al., Assays of endogenous caspase activities: a comparison of mass spectrometry and fluorescence formats, Anal. Chem., 78(14):4945-51 (Jul. 2006).

(56) References Cited

OTHER PUBLICATIONS

Su et al., Combining Microfluidic Networks and Peptide Arrays for Multi-Enzyme Assays, Journal of American Chemical Society, Journal of the American Chemical Society, 127:7280-7281 (2005).
Su et al., Using MALDI-TOF mass spectrometry to characterize interfacial reactions on self-assembled monolayers. *Langmuir*, 19: 4867-70 (2003).
Su et al., Using mass spectrometry to characterize self-assembled monolayers presenting peptides, proteins, and carbohydrates, Angew. Chem. Int. Ed. Engl., 41(24):4715-8 (Dec. 2002).
Ting et al., "Genetically encoded fluorescent reporters of protein tyrosine kinase activities in living cells," Proc Natl Acad Sci U S A 98:15003-15008 (2001).
Tsien et al., "The Green Fluorescent Protein," Annu. Rev. Biochem. 67:509-544 (1998).
Tsubery et al., Biochemical assays of immobilized oligonucleotides with mass spectrometry, Langmuir, 24(10):5433-8 (May 2008).
Wehrman et al., "Enzymatic detection of protein translocation," Nat. Methods, 2(7):521-527 (2005).
Whitney et al., "A Genome-Wide Functional Assay of Signal Transduction in Living Mammalian Cells," Nat. Biotechnol., 16:1329-1333 (1998).
Yeo et al., Electroactive monolayer substrates that selectively release adherent cells. *Chembiochem*. 2: 590-3 (2001).
Yeo et al., Electroactive substrates that reveal aldehyde groups for bio-immobilization. *Adv Mater*. 16: 1352-6 (2004).
Yeo et al., Label-free detection of protein-protein interactions on biochips, Angew. Chem. Int. Ed. Engl., 44(34):5480-3 (Aug. 2005).
Yeo et al., Self-assembled monolayers that transduce enzymatic activities to electrical signals. *Angew. Chem. Int. Ed. Engl.* 42: 3121-4 (2003).
Yonzon et al., A comparative analysis of localized and propagating surface plasmon resonance sensors: the binding of concanavalin a to a monosaccharide functionalized self-assembled monolayer. *J. Am. Chem. Soc.* 126: 12669-76 (2004).
Yousaf et al., Diels-Alder Reaction for the selective immobilization of protein to electroactive self-assembled monolayers. J. Am. Chem. Soc. 121: 4286-7 (1999).
Yousaf et al., Electroactive substrates that modulate cell growth, Biochemistry, 39(6): Abstract 170, p. 1580 (2000).
Yousaf et al., The kinetic order of an interfacial diels-Alder Reaction depends on the environment of the immobilized dienophile. *Angew. Chem. Int. Ed. Engl.* 39: 1943-6 (2000).
Yousaf et al., Turning on cell migration with electroactive substrates. *Angew. Chem. Int. Ed. Engl.* 40: 1093-6 (2001).
Yousaf et al., Using electroactive substrates to pattern the attachment of two different cell populations. *Proc. Natl. Acad. Sci. USA*, 98: 5992-6 (2001).
Zhang et al., "A Simple Statistical Parameter for Use in Evaluation and Validation of High Throughput Screening Assays," J Biomol Screen 4:67-73 (1999).
Zhang et al., "Genetically encoded reporters of protein kinase A activity reveal impact of substrate tethering," Proc Natl Acad Sci U S A 98:14997-15002 (2001).
Zhu et al., Grafting of High-Density Poly(Ethylene Glycol) Monolayers on Si(111), American Chemical Society, Langmuir, 17(25):7798-7803 (Sep. 2001).
Zlokarnik et al., "Quantitation of transcription and clonal selection of single living cells with beta-lactamase as reporter," Science, 279:84-88 (1998).

* cited by examiner

TRACELESS IMMOBILIZATION OF ANALYTES FOR SAMDI MASS SPECTROMETRY

CROSS-REFERENCE TO RELATED APPLICATION

This application is a U.S. National Phase of PCT/US19/36081, filed Jun. 7, 2019, which claims the priority benefit under 35 U.S.C. § 119 (e) of U.S. Provisional Patent Application No. 62/657,441, filed Apr. 13, 2018, the disclosures of which are incorporated herein by reference in their entirety.

STATEMENT OF GOVERNMENT INTEREST

This invention was made with government support under grant number FA8650-15-2-5518 awarded by the Air Force Research Lab (AFRL). The government has certain rights in the invention.

FIELD OF THE INVENTION

The present disclosure is directed to materials and methods of high throughput, traceless immobilization of analytes for use in self-assembled monolayer for matrix-assisted laser desorption and ionization (SAMDI) mass spectrometry. Methods of the disclosure are useful, in various embodiments, for measuring the activity of an enzyme or for monitoring a chemical reaction.

BACKGROUND

Several recent reports have illustrated the benefits of applying high-throughput experiments to develop, optimize, and understand reactions.[1-3] Yet, current methods rely on labels to analyze the reactions, limiting the activities that can be assayed and introducing artifacts, or on chromatography with a significant loss in throughput. Mass spectrometry, particularly when combined with surface chemistries, allows for high-throughput assays of chemical and biochemical reactions.[4] Development of the SAMDI (self-assembled monolayer for matrix-assisted laser desorption and ionization) method uses self-assembled monolayers of alkanethiolates on gold to immobilize analytes that can then be quantitated with mass spectrometry. SAMDI has been particularly important in enabling rapid and quantitative analysis of enzyme activities.[5] In the SAMDI method, substrates are either first immobilized to the monolayer and treated with an enzyme,[6-13] or treated with the enzyme in a solution-phase reaction and subsequently immobilized to the monolayer prior to analysis by mass spectrometry.[7, 8, 14-16] In either case, the substrate must be modified with a functional group that allows its immobilization.[16] While this requirement for an immobilization tag is often not problematic, there are cases where the introduction of the tag is either not straightforward or is incompatible with the activity to be measured. SAMDI has also been used in the discovery and study of reactions, and here too the need for a functional group can interfere with the intended reaction.[24, 25]

SUMMARY

In some aspects, the disclosure provides a self-assembled monolayer-substrate composition, comprising: a self-assembled monolayer (SAM) attached to at least a portion of the substrate surface, wherein the SAM comprises an alkyl chain having a reactive group at one terminus for association with the substrate surface and at least a portion of the SAM further comprising a traceless linker that is capable of reacting with an analyte upon exposure to ultraviolet light. In some embodiments, the SAM comprises the alkyl chain and a spacer group, with at least a portion of the SAM further comprising the traceless linker. In further embodiments, the spacer comprises two to twenty ethylene glycol groups. In some embodiments, the spacer has a structure of

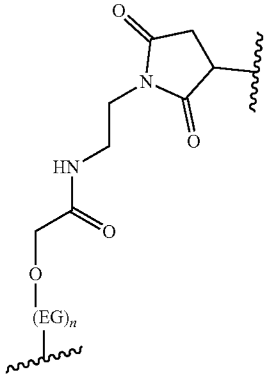

wherein EG is ethylene glycol, and n is 2-20. In further embodiments, n is 2-5. In some embodiments, the spacer is an alkyl spacer, a peptidic spacer, or a 6-aminohexanoic acid spacer.

In some embodiments, the traceless linker comprises a diazirine. In further embodiments, the traceless linker comprises 3-trifluoromethyl-3-phenyl-diazirine (TPD). In still further embodiments, the traceless linker forms a carbene upon exposure to ultraviolet light.

In some embodiments, the substrate surface comprises gold. In further embodiments, the substrate surface comprises silver. In still further embodiments, the substrate surface comprises copper.

In various embodiments, the density of traceless linker is from about 0.1% to 100%. In some embodiments, the density of traceless linker is from about 10% to about 50%. In further embodiments, the density of traceless linker is at least about 10%, while in still further embodiments the density of traceless linker is at least about 20%.

In some embodiments, the traceless linker is attached to the SAM via reaction of complementary reactive groups on the SAM and on the traceless linker. In further embodiments, the complementary reactive groups comprise an azide, an alkyne, a maleimide, a thiol, an alcohol, an amine, a carboxylic acid, an olefin, an isothiocyanate, a N-hydroxysuccinimide, a phosphine, a nitrone, a norbornene, an oxanorbornene, a transcycloctene, an s-tetrazene, an isocyanide, a tetrazole, a nitrile oxide, a quadricyclane, or a carbodiimide. Thus, in some embodiments the traceless linker is directly attached to the SAM.

In some aspects, the disclosure provides a method of making a composition of the disclosure comprising contacting the substrate with the alkyl chain having a reactive group at one terminus to attach the alkyl chain to at least a portion of the substrate surface to form the SAM, wherein at least a portion of alkyl chains of the SAM further comprise a spacer group and/or a reactive group at the opposite terminus to attach the traceless linker, and contacting the reactive group and the traceless linker to attach the traceless linker via a complementary reactive group on the traceless linker. In some embodiments, the reactive group on the traceless linker comprises a maleimide. In further embodiments, the reactive group on the alkyl chain or the reactive group on the traceless linker comprises an azide, an alkyne, a maleimide, a thiol, an alcohol, an amine, a carboxylic acid, an olefin, an isothiocyanate, a N-hydroxysuccinimide, a phosphine, a nitrone, a norbornene, an oxanorbornene, a transcyclooctene, an s-tetrazene, an isocyanide, a tetrazole, a nitrile oxide, a quadricyclane, or a carbodiimide to react with the maleimide. In some embodiments, the method further comprises contacting the composition and an analyte under ultraviolet light to attach the analyte. In some embodiments, the traceless linker comprises a diazirine and the ultraviolet light forms a carbene which reacts with the analyte. In further embodiments, the analyte comprises a protein, a peptide, an antibody, an oligonucleotide, a small molecule, a carbohydrate, an amino acid, a fatty acid, a metabolite, a lipid, a drug, or a reaction product.

In some aspects, a method of measuring activity of an enzyme is provided, comprising (a) contacting the enzyme with an enzyme analyte to form a reaction mixture; wherein the enzyme analyte, upon contact with the enzyme, forms a product, such that the enzyme analyte and the product comprise different masses; (b) contacting the reaction mixture of (a) with a composition of the disclosure such that the enzyme analyte and the product are attached to the composition via reaction with the traceless linker in the presence of ultraviolet light; (c) subjecting the composition to mass spectrometry to produce a mass spectrum having an enzyme analyte signal and an product signal; and (d) measuring the activity of the enzyme by correlating a signal intensity of the enzyme analyte signal to a signal intensity of the product signal to determine the extent of product formation and thereby measuring the activity of the enzyme. In some embodiments, the enzyme is a deacetylase, acetyltransferase, esterase, phosphorylase/kinase, phosphatase, protease, methylase, demethylase, or a DNA or RNA modifying enzyme. In further embodiments, the deacetylase is KDAC8. In some embodiments, the esterase is cutinase or acetylcholine esterase. In further embodiments, the protease is TEV. In some embodiments, the enzyme analyte comprises an acylated peptide and the product comprises a deacylated peptide. In some embodiments, the enzyme analyte comprises a deacylated peptide and the product comprises an acylated peptide. In some embodiments, the enzyme analyte comprises a phosphorylated peptide and the product comprises a dephosphorylated peptide. In further embodiments, the enzyme analyte comprises a dephosphorylated peptide and the product comprises a phosphorylated peptide. In some embodiments, the enzyme analyte comprises a methylated peptide and the product comprises a demethylated peptide. In further embodiments, the enzyme analyte comprises a demethylated peptide and the product comprises a methylated peptide.

In some aspects, the disclosure provides a method of monitoring a chemical reaction, comprising (a) contacting two or more reactants of the chemical reaction to form a reaction mixture; wherein the two or more reactants, upon contact, forms a product, such that the reactants and the product comprise different masses; (b) contacting the reaction mixture of (a) with a composition of the disclosure such that the reactant and the product are attached to the composition via reaction with the traceless linker in the presence of ultraviolet light; (c) subjecting the composition to mass spectrometry to produce a mass spectrum having a product signal and reactant signals, one for each reactant; and (d) monitoring the chemical reaction by correlating a signal intensity of at least one of the reactant signals to a signal intensity of the product signal to determine the extent of product formation and thereby monitoring the chemical reaction. In some embodiments, the chemical reaction is a Suzuki reaction, and the two or more reactants comprise an organoboron and a halide compound.

DETAILED DESCRIPTION

Label-free assays, and particularly those based on the combination of mass spectroscopy with surface chemistries, enable high-throughput experiments of a broad range of reactions. However, these methods still require the incorporation of functional groups that allow immobilization of reactants and products to surfaces prior to analysis. In some aspects, the disclosure provides traceless methods for attaching molecules to a self-assembled monolayer for matrix-assisted laser desorption and ionization (SAMDI) mass spectrometry. In some embodiments, the methods use monolayers that are functionalized with a 3-trifluoromethyl-3-phenyl-diazirine (TPD) that liberates nitrogen when irradiated and gives a carbene that inserts into a wide range of molecules. Analysis of the monolayer with SAMDI then reveals peaks for each of the adducts formed from molecules in the sample. Applications of the methods of the disclosure include, but are not limited to, assays to quantify enzyme activity, reaction and catalyst discovery, drug metabolism, and small molecule detection. In specific embodiments, methods of the disclosure are applied to characterize a P450 drug metabolizing enzyme or to monitor a Suzuki-Myaura coupling chemical reaction.

Traceless linkers. In any of the aspects or embodiments of the disclosure, a self-assembled monolayer-substrate composition is provided that comprises a traceless linker that is capable of reacting with an analyte upon exposure to ultraviolet light. In some embodiments, the traceless linker comprises a diazirine. In further embodiments, the traceless linker comprises 3-trifluoromethyl-3-phenyl-diazirine (TPD). In still further embodiments, the traceless linker forms a carbene upon exposure to ultraviolet light. In some embodiments, the traceless linker comprises benzophenone. In further embodiments, the traceless linker comprises an aryl azide, an azido-methyl-coumarin, an anthraquinone, a diazo compound, a diazirine, or a psoralen derivative.

Figure 1:
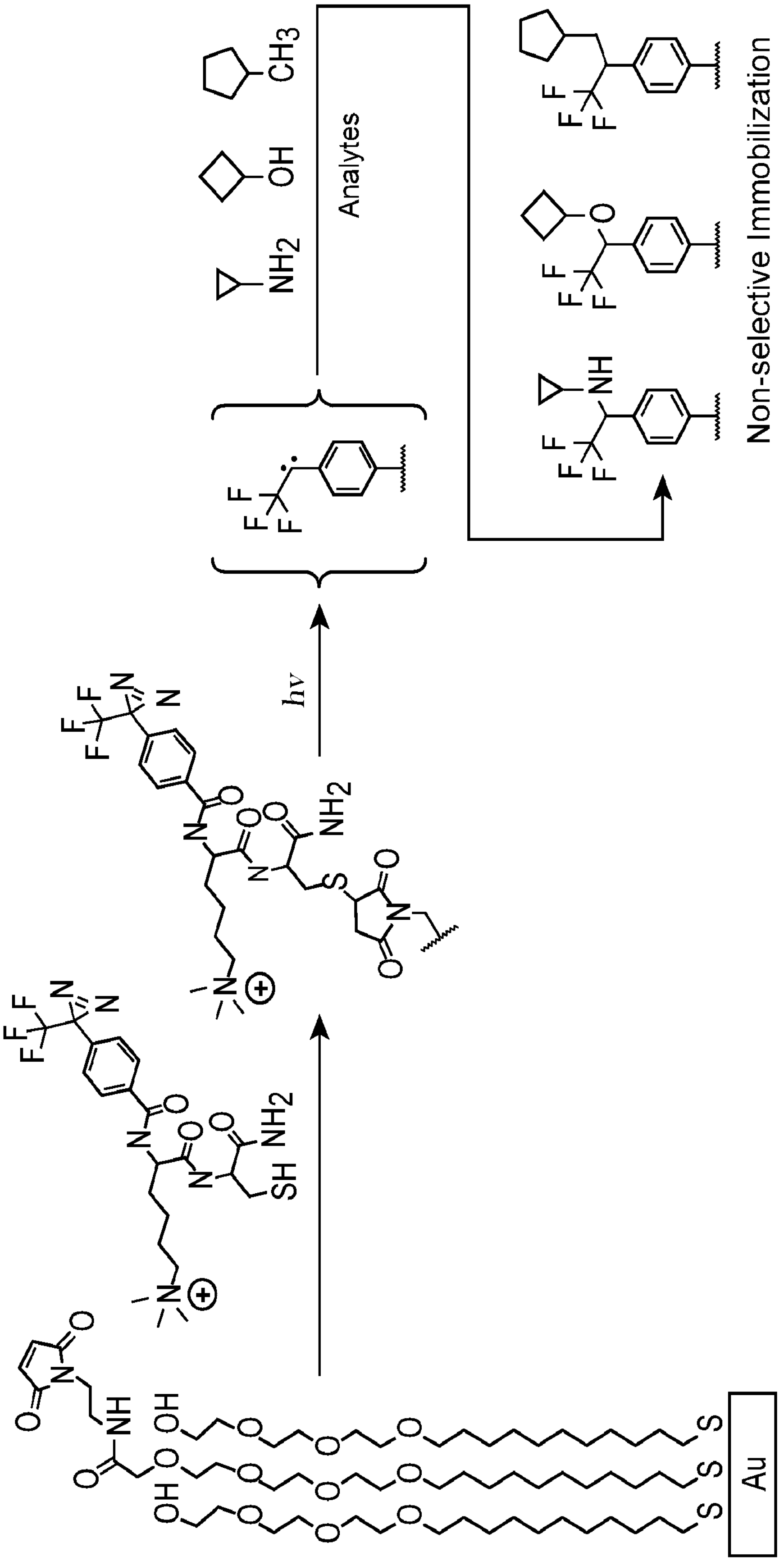
FIG. 1 shows an overview of the TI-SAMDI-MS method. A TPD is immobilized to a monolayer presenting maleimide groups against a background of tri (ethylene glycol) groups. Subsequent application of a solution containing analytes and exposure to ultraviolet light results in the photo-generation of a reactive carbene and covalent attachment of analytes, which can subsequently be identified with SAMDI-MS. The analytes can react at multiple bonds to give a mixture of isomeric products.

Self-Assembled Monolayer Substrates. The present disclosure contemplates the use of self-assembled monolayers as substrates for assay applications (Mrksich et al., Annu Rev Biophys Biomol Struct 25:55-78 (1996); Hodneland et al., Langmuir 13:6001-6003 (1997); Houseman et al., FASEB J 11: A1095-A1095 (1997); Mrksich, Curr Opin Colloid In 2:83-88 (1997); Mrksich et al., Acs Sym Ser 680:361-373 (1997); Houseman et al., Mol Biol Cell 9: 430a-430a (1998); Mrksich, Cell Mol Life Sci 54:653-662 (1998); Houseman et al., Angew Chem Int Ed 38:782-785 (1999); Li et al., Langmuir 15:4957-4959 (1999); Yousaf et al., J Am Chem Soc 121:4286-4287 (1999); Houseman et al., Mol Biol Cell 11: 45a-45a (2000); Luk et al., Langmuir 16:9604-9608. (2000); Mrksich, Chem Soc Rev 29:267-273 (2000); Yousaf et al., Angew Chem Int Ed Engl 39:1943-1946 (2000); Yousaf et al., Biochemistry 39:1580-1580 (2000); Houseman et al., Biomaterials 22:943-955 (2001); Kato et al., Biochemistry 40:8608-8608 (2001); Yeo et al., Chembiochem 2:590-593 (2001); Yousaf et al., Proc Natl Acad Sci USA 98:5992-5996. (2001); Yousaf et al., Angew Chem Int Ed Engl 40:1093-1096 (2001); Hodneland et al., Proc Natl Acad Sci USA 99:5048-5052 (2002); Houseman et al., Nat Biotechnol 20:270-274 (2002); Houseman et al., Top Curr Chem 218:1-44 (2002); Houseman et al., Trends Biotechnol 20:279-281 (2002); Houseman et al., Chem Biol 9:443-454 (2002); Kwon et al., J Am Chem Soc 124:806-812 (2002); Lee et al., Science 295:1702-1705 (2002); Mrksich, Curr Opin Chem Biol 6:794-797 (2002); Houseman et al., Langmuir 19:1522-1531 (2003); Luk et al., Biochemistry 42:8647-8647 (2003); Yeo et al., Angew Chem Int Ed Engl 42:3121-3124 (2003); Dillmore et al., Langmuir 20:7223-7231 (2004); Feng et al., Biochemistry 43:15811-15821 (2004); Kato et al., J Am Chem Soc 126: 6504-6505 (2004); Min et al., Curr Opin Chem Biol 8:554-558 (2004); Murphy et al., Langmuir 20:1026-1030 (2004); Yeo et al., Adv Mater 16:1352-1356 (2004); Yonzon et al., J Am Chem Soc 126:12669-12676 (2004); Mrksich, MRS Bull 30:180-184 (2005); James et al., Cell Motil Cytoskeleton 65:841-852 (2008)). Specifically, the disclosure provides, in some aspects, a self-assembled monolayer-substrate composition, comprising: a self-assembled monolayer (SAM) attached to at least a portion of the substrate surface, wherein the SAM comprises an alkyl chain having a reactive group at one terminus for association with the substrate surface and at least a portion of the SAM further comprising a traceless linker that is capable of reacting with an analyte upon exposure to ultraviolet light. In some embodiments, the SAM comprises the alkyl chain and a spacer group, with at least a portion of the SAM further comprising the traceless linker. The traceless linker is, in various embodiments, on the terminus of the alkyl chain that is opposite the reactive group that associates the alkyl chain with the substrate surface. In further embodiments, the spacer comprises two to twenty ethylene glycol groups. See FIG. 1.

Previous work utilized a monolayer that presented a peptide against a background of tri (ethylene glycol) groups (Houseman et al., Nat Biotechnol 20:270-274 (2002)). The peptide was a substrate for Src kinase and the glycol groups prevented non-specific adsorption of protein to the monolayer. Treatment of the monolayer with enzyme and ATP resulted in phosphorylation of the peptide, which was detected by measuring radioactivity from a $^{32}$P label or by using an anti-phosphotyrosine antibody with detection by fluorescence scanning or surface plasmon resonance spectroscopy. This example showed that the use of monolayers gave solid-phase assay with exceptional performance. It further indicated that blocking procedures were unnecessary; the signal was 80-fold above background; and that enzyme constants and inhibitor dissociation constants could be measured quantitatively. The monolayers offer the benefits that immobilized ligands are presented in a homogeneous environment and the density of the immobilized ligands can be controlled and made uniform across the entire array (Gawalt et al., J Am Chem Soc 126:15613-7 (2004)). The monolayers are also compatible with a range of immobilization chemistries (Montavon et al., Nat Chem 4:45-51 (2012); Ban et al., Nat Chem Biol 8:769-773 (2012); Li et al., Langmuir 23, 11826-11835 (2007)). In these respects, the monolayers are more effective as substrates in assay applications than is the nitrocellulose material (or even the common use of glass). A significant additional benefit of the monolayer substrates is that they can be analyzed by matrix-assisted laser desorption-ionization mass spectrometry (i.e., SAMDI mass spectrometry) and therefore provide a route to label-free assays of biochemical activities (Su et al., Langmuir 19:4867-4870 (2003)).

Methods of making a composition of the disclosure are also provided herein. Such methods comprise contacting a substrate with an alkyl chain having a reactive group at one terminus to attach the alkyl chain to at least a portion of the substrate surface to form the SAM, wherein at least a portion of alkyl chains of the SAM further comprise a spacer group and/or a reactive group at the opposite terminus to attach the traceless linker, and contacting the reactive group and the traceless linker to attach the traceless linker via a complementary reactive group on the traceless linker. In some embodiments, the reactive group on the traceless linker comprises a maleimide. In further embodiments, the reactive group on the alkyl chain or the reactive group on the traceless linker comprises an azide, an alkyne, a maleimide, a thiol, an alcohol, an amine, a carboxylic acid, an olefin, an isothiocyanate, a N-hydroxysuccinimide, a phosphine, a nitrone, a norbornene, an oxanorbornene, a transcycloctene, an s-tetrazene, an isocyanide, a tetrazole, a nitrile oxide, a quadricyclane, or a carbodiimide to react with the maleimide. In some embodiments, the method further comprises contacting the composition and an analyte under ultraviolet light to attach the analyte. In some embodiments, the traceless linker comprises a diazirine and the ultraviolet light forms a carbene which reacts with the analyte. In further embodiments, the analyte comprises a protein, a peptide, an antibody, an oligonucleotide, a small molecule, a carbohydrate, an amino acid, a fatty acid, a metabolite, a lipid, a drug, or a reaction product.

Spacer. As disclosed herein, in some embodiments the self-assembled monolayer-substrate composition comprises a spacer. In various embodiments, the composition comprises a substituted alkanethiol, which comprises a thiol, an alkyl chain, and then a spacer and traceless linker (e.g., a photoreactive group). See FIG. 1. In some embodiments, the spacer is an ethylene glycol moiety comprising two to twenty ethylene glycol groups. In some embodiments, the spacer has a structure of

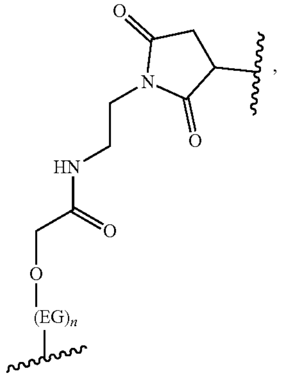

wherein EG is ethylene glycol, and n is 2-20. In some embodiments, n is 2-5.

In further embodiments, the spacer is an alkyl spacer, a peptidic spacer, or a 6-aminohexanoic acid spacer.

SAMDI Mass Spectrometry

Methods of the disclosure are based on the SAMDI mass spectrometry technique (U.S. Patent Application Publication Number 2010/0112722, incorporated herein by reference in its entirety) and use matrix-assisted laser desorption-ionization mass spectrometry to analyze self-assembled monolayers. SAMDI mass spectrometry can be used to detect the mass of a analyte or product. In this way, when the monolayer is treated with an enzyme that modifies the immobilized analyte, the resulting mass change of the immobilized product can be detected with mass spectrometry. The assay is applicable to a broad range of post-translational activities, can be performed in high throughput using plates having a number of distinct reaction zones (e.g., 1536) offering a throughput of about 50,000 assays per day, and is quantitative with Z-factors greater than 0.8. The assay can also be used to screen small molecule libraries to identify inhibitors or activators of enzymes.

In SAMDI, the monolayer is irradiated with a laser, which results in desorption of the products and analytes through dissociation of a thiolate-gold bond, but with little fragmentation of these molecules. Hence, the resulting spectra are straightforward to interpret. Assays using this SAMDI technique can be used on a range of enzyme activities, and are quantitative, compatible with complex lysates, and adaptable to high throughput formats (Ban et al., Nat Chem Biol 8:769-773 (2012); Li et al., Langmuir 23:11826-11835 (2007); Su et al., Langmuir 19:4867-4870 (2003); Su et al., Angew Chem Int Ed Eng. 41:4715-4718 (2002); Min et al., Angewandte Chemie 43:5973-5977 (2004); Min et al., Anal Chem 76:3923-3929 (2004); Yeo et al., Angew Chem Int Ed Engl 44:5480-5483 (2005); Marin et al., Angew Chem Int Ed Engl 46:8796-8798 (2007); Patrie et al., Anal Chem 79:5878-5887 (2007); Ban et al., Angew Chem Int Ed Eng 47:3396-3399 (2008); Gurard-Levin et al., Annu Rev Anal Chem (Palo Alto Calif) 1:767-800 (2008); Gurard-Levin et al., Biochemistry 47:6242-6250 (2008); Mrksich, ACS Nano 2:7-18 (2008); Tsubery et al., Langmuir 24:5433-5438 (2008); Gurard-Levin et al., Chembiochem 10:2159-2161 (2009); Liao et al., Chemistry 15, 12303-12309 (2009); Gurard-Levin et al., ACS Chem Biol 5:863-873 (2010); Kim et al., Nucleic Acids Res 38: e2 (2010); Cai et al., Carbohydr Res 346:1576-1580 (2011); Gurard-Levin et al., ACS Comb Sci 13:347-350 (2011); Liao et al., Angew Chem Int Ed Engl 50:706-708 (2011); Prats-Alfonso et al., Small 8:2106-2115 (2012); Li et al., Langmuir 29:294-298 (2013)).

The methods described herein offer several advantages over existing technologies. First, the methods of the disclosure improve mass-spectroscopy enzyme assays by allowing for analysis of unmodified analytes in solution. Second, methods of the disclosure differentiate from other label-free methods such as LC-MS (liquid chromatography mass spectrometry) and HPLC (high performance liquid chromatography) methods by a greater throughput of small molecule analysis.

As used herein, the "density" of traceless linker on the substrate refers to the fraction of alkyl chains attached to the substrate surface that are modified to comprise a traceless linker. In some embodiments, the density of traceless linker on the substrate is from about 0.1% to about 100%. In further embodiments, the density of traceless linker on the substrate is from about 0.1% to about 100%, or from about 5% to about 90%, or from about 5% to about 80%, or from about 5% to about 70%, or from about 5% to about 60%, or from about 5% to about 50%, or from about 5% to about 40%, or from about 5% to about 30%, or from about 5% to about 20%, or from about 5% to about 10%. In further embodiments, the density of traceless linker on the substrate is from about 10% to about 90%, or from about 10% to about 80%, or from about 10% to about 70%, or from about 10% to about 60%, or from about 10% to about 50%, or from about 10% to about 40%, or from about 10% to about 30%, or from about 10% to about 20%. In some embodiments, the total density of traceless linker on the substrate is less than or equal to about 50%. In some embodiments, the total density of the traceless linker on the substrate is less than or equal to about 49%, or is less than or equal to about 48%, or is less than or equal to about 48%, or is less than or equal to about 48%, or is less than or equal to about 48%, or is less than or equal to about 47%, or is less than or equal to about 46%, or is less than or equal to about 45%, or is less than or equal to about 44%, or is less than or equal to about 43%, or is less than or equal to about 42%, or is less than or equal to about 41%, or is less than or equal to about 40%, or is less than or equal to about 39%, or is less than or equal to about 38%, or is less than or equal to about 37%, or is less than or equal to about 36%, or is less than or equal to about 35%, or is less than or equal to about 34%, or is less than or equal to about 33%, or is less than or equal to about 32%, or is less than or equal to about 31%, or is less than or equal to about 30%, or is less than or equal to about 29%, or is less than or equal to about 28%, or is less than or equal to about 27%, or is less than or equal to about 26%, or is less than or equal to about 25%, or is less than or equal to about 24%, or is less than or equal to about 23%. In some embodiments, the total density of the traceless linker on the substrate is less than or equal to about 19%, or is less than or equal to about 18%, or is less than or equal to about 17%, or is less than or equal to about 16%, or is less than or equal to about 15%, or is less than or equal to about 14%, or is less than or equal to about 13%. In some embodiments, the total density of the traceless linker on the substrate is less than or equal to about 9%, or is less than or equal to about 8%, or is less than or equal to about 7%, or is less than or equal to about 6%, or is less than or equal to about 5%, or is less than or equal to about 4%, or is less than or equal to about 3%. In additional embodiments, the total density of the traceless linker on the substrate is from about 3% to about 7%, or from about 4% to about 7%, or from about 5% to about 7%, or from about 3% to about 6%, or from about 4% to about 6%, or from about 5% to about 6%. In further embodiments, the total density of the traceless linker on the substrate is or is at least 1%, is or is at least 2%, is or is at least 5%, is or is at least 6%, is or is at least 7%, is or is at least 8%, is or is at least 9%, is or is at least 10%, is or is at least 15%, is or is at least 20%, is or is at least 25%, is or is at least 30%, is or is at least 35%, is or is at least 40%, is or is at least 50%, is or is at least 60%, is or is at least 70%, is or is at least 80%, is or is at least 90%, or is or is at least 95%.

Substrate Surface. In any of the aspects or embodiments of the disclosure, a substrate as disclosed herein comprises a surface. The substrate surface can be any material capable of forming a monolayer, e.g., a monolayer of alkanethiols. Particularly, the substrate surface may be a metal, such as Au, Ag, Pd, Pt, Cu, Zn, Fe, In, Si, $Fe_2O_3$, $SiO_2$ or ITO (indium tin oxide) glass. In various embodiments, the disclosure contemplates that a substrate surface useful in the methods described herein comprises Au, Ag, or Cu.

Reactive Groups. As disclosed herein, the SAM comprises an alkyl chain having a reactive group at one terminus for association with the substrate surface and at least a portion of the SAM further comprising a traceless linker that is capable of reacting with an analyte upon exposure to ultraviolet light. In any of the embodiments of the disclosure, the SAM comprises an alkyl chain having a reactive group at both termini: at the first terminus, the reactive group is for attachment of the alkyl chain to the substrate surface, while at the second terminus the reactive group is for immobilizing the traceless linker, wherein the traceless linker comprises a reactive group that is complementary to the reactive group on the second terminus of the alkyl chain. In some embodiments, the reactive group is a thiol group. In further embodiments, the reactive group comprises an azide, an alkyne, a maleimide, a thiol, an alcohol, an amine, a carboxylic acid, an olefin, an isothiocyanate, a N-hydroxysuccinimide, a phosphine, a nitrone, a norbornene, an oxanorbornene, a transcycloctene, an s-tetrazene, an isocyanide, a tetrazole, a nitrile oxide, a quadricyclane, or a carbodiimide.

Analyte. In various aspects and embodiments of the disclosure, methods include the use of an analyte. As used herein, the term "analyte" includes a protein (e.g., an enzyme), a peptide, an antibody, an oligonucleotide, a small molecule, a carbohydrate, an amino acid, a fatty acid, a metabolite, a lipid, a drug, or a reaction product. In various embodiments, the enzyme is a deacetylase, acetyltransferase, esterase, phosphorylase/kinase, phosphatase, protease, methylase, demethylase, oxidoreductase, transferase, hydrolase, lipase, lyase, ligase, cytochrome P450, cellulase, or a DNA or RNA modifying enzyme.

As used herein a "protein" refers to a polymer comprised of amino acid residues and may also be referred to as a "polypeptide" in the art. Consistent with the understanding in the art, "protein" can also refer to the association (covalent or non-covalent) of distinct "polypeptide" or "protein" polymers or chains.

Proteins of the present disclosure may be either naturally occurring or non-naturally occurring.

Naturally occurring proteins include, without limitation, biologically active proteins (including antibodies) that exist in nature or can be produced in a form that is found in nature by, for example, chemical synthesis or recombinant expression techniques. Naturally occurring proteins also include lipoproteins and post-translationally modified proteins, such as, for example and without limitation, glycosylated proteins.

Antibodies contemplated for use in the methods and compositions of the present disclosure include without limitation antibodies that recognize and associate with a target molecule either in vivo or in vitro.

Structural polypeptides contemplated by the disclosure include without limitation actin, tubulin, collagen, elastin, myosin, kinesin and dynein.

Non-naturally occurring proteins contemplated by the present disclosure include but are not limited to synthetic proteins, as well as fragments, analogs and variants of naturally occurring or non-naturally occurring proteins as defined herein. Non-naturally occurring proteins also include proteins or protein substances that have D-amino acids, modified, derivatized, or non-naturally occurring amino acids in the D- or L-configuration and/or peptidomimetic units as part of their structure.

Non-naturally occurring proteins are prepared, for example, using an automated polypeptide synthesizer or, alternatively, using recombinant expression techniques using a modified polynucleotide that encodes the desired protein.

As used herein a "fragment" of a protein is meant to refer to any portion of a protein smaller than the full-length protein expression product.

As used herein an "analog" refers to any of two or more proteins substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physico-chemical or functional relatedness of the amino acid that is being replaced and the amino acid replacing it.

As used herein a "variant" refers to a protein or analog thereof that is modified to comprise additional chemical moieties not normally a part of the molecule. Such moieties may modulate, for example and without limitation, the molecule's solubility, absorption, and/or biological half-life. Moieties capable of mediating such effects are disclosed in Remington's Pharmaceutical Sciences (1980). Procedures for coupling such moieties to a molecule are well known in the art. In various aspects, polypeptides are modified by glycosylation, PEGylation, and/or polysialylation.

In some embodiments, enzymes useful in the methods of the disclosure include a cytochrome P450 (CYP) enzyme. CYPs are a family of isozymes responsible for the biotransformation of several drugs (see, e.g., Ogu et al., Proc (Bayl Univ Med Cent). 2000 October; 13 (4): 421-423). The enzymes are heme-containing membrane proteins, which are located in the smooth endoplasmic reticulum of several tissues. Although a majority of the isozymes are located in the liver, extrahepatic metabolism also occurs in the kidneys, skin, gastrointestinal tract, and lungs. The highest expressed forms in liver are CYPs 3A4, 2C9, 2C8, 2E1, and 1A2, while 2A6, 2D6, 2B6, 2019 and 3A5 are less abundant and CYPs 2J2, 1A1, and 1B1 are mainly expressed extrahepatically. Significant inactivation of some orally administered drugs is due to the extensive first-pass metabolism in the gastrointestinal tract by the CYP3A4 isozyme.

As disclosed and exemplified herein, methods of the disclosure are useful in measuring the activity of an enzyme. The method comprises (a) contacting the enzyme with an enzyme analyte to form a reaction mixture; wherein the enzyme analyte, upon contact with the enzyme, forms a product, such that the enzyme analyte and the product comprise different masses; (b) contacting the reaction mixture of (a) with a composition of the disclosure such that the enzyme analyte and the product are attached to the composition via reaction with the traceless linker in the presence of ultraviolet light; (c) subjecting the composition to mass spectrometry to produce a mass spectrum having an enzyme analyte signal and an product signal; and (d) measuring the activity of the enzyme by correlating a signal intensity of the enzyme analyte signal to a signal intensity of the product signal to determine the extent of product formation and thereby measuring the activity of the enzyme. In some embodiments, the enzyme analyte comprises an acylated peptide and the product comprises a deacylated peptide. In some embodiments, the enzyme analyte comprises a deacylated peptide and the product comprises an acylated peptide. In further embodiments, the enzyme analyte comprises a phosphorylated peptide and the product comprises a dephosphorylated peptide. In some embodiments, the enzyme analyte comprises a dephosphorylated peptide and the product comprises a phosphorylated peptide. In further embodiments, the enzyme analyte comprises a methylated peptide and the product comprises a demethylated peptide. In some embodiments, the enzyme analyte comprises a demethylated peptide and the product comprises a methylated peptide.

KDAC as a Reporter Enzyme. In some embodiments of the disclosure, the lysine deacetylase KDAC8 is utilized as a reporter enzyme. This enzyme can deacetylate appropriate peptide analytes on a monolayer and it has been shown that the assay works well in cell lysate. Further, a high throughput screen of inhibitors has been performed for this enzyme and the screen was shown to be of high quality (the Z'-factor was 0.84) (Gurard-Levin et al., Biochemistry 47:6242-6250 (2008); Gurard-Levin et al., Chembiochem 10:2159-2161 (2009); Gurard-Levin et al., ACS Chem Biol 5:863-873 (2010); Gurard-Levin et al., ACS Comb Sci 13:347-350 (2011); Mwakwari et al., J Med Chem 53:6100-6111 (2010); Patil et al., J Med Chem 56:3492-3506 (2013)).

Modulators/Activators. Some aspects of the disclosure provide a method of assaying a modulator of enzyme activity. The methods comprise (a) contacting the enzyme with an enzyme analyte to form a reaction mixture; wherein the enzyme analyte, upon contact with the enzyme, forms a product, such that the enzyme analyte and the product comprise different masses; (b) contacting the reaction mixture of (a) with a composition as described herein such that the enzyme analyte and the product are attached to the composition via reaction with the traceless linker in the presence of ultraviolet light; (c) subjecting the composition to mass spectrometry to produce a mass spectrum having an enzyme analyte signal and a product signal; and (d) measuring the activity of the enzyme by correlating a signal intensity of the enzyme analyte signal to a signal intensity of the product signal to determine the extent of product formation and thereby measuring the activity of the enzyme. In some embodiments, the enzyme analyte and the enzyme are contacted in the presence of one or more potential modulators of the enzyme-analyte interaction; subjecting the enzyme analyte and product to mass spectrometry to produce a mass spectrum having a product signal and an enzyme analyte signal; and measuring activity of the enzyme by correlating a signal intensity of the product to a signal intensity of the enzyme analyte to determine the extent of product formation and thereby detecting the activity of the enzyme in the presence of the one or more potential modulators.

In some embodiments, the modulator is an inhibitor of enzyme activity. In further embodiments, the modulator is an activator of enzyme activity.

Monitoring a Chemical Reaction. Additional aspects of the disclosure comprise methods of monitoring a chemical reaction. "Monitor" is used herein to mean that the methods detect the conversion of one or more reactants into a product. In some embodiments, such methods comprise (a) contacting two or more reactants of the chemical reaction to form a reaction mixture; wherein the two or more reactants, upon contact, forms a product, such that the reactants and the product comprise different masses; (b) contacting the reaction mixture of (a) with a composition of the disclosure such that the reactant and the product are attached to the composition via reaction with the traceless linker in the presence of ultraviolet light; (c) subjecting the composition to mass spectrometry to produce a mass spectrum having a product signal and reactant signals, one for each reactant; and (d) monitoring the chemical reaction by correlating a signal intensity of at least one of the reactant signals to a signal intensity of the product signal to determine the extent of product formation and thereby monitoring the chemical reaction.

In some embodiments, the chemical reaction is a Suzuki reaction, and the two or more reactants comprise an organoboron and a halide compound.

EXAMPLES

To enable assays in a true 'label-free' format, a general strategy termed Traceless Immobilization SAMDI-MS (TI-SAMDI-MS) (FIG. 1) is described herein and below that uses a photo-generated carbene to non-selectively attach molecules to the monolayer, where they can then be analyzed by mass spectrometry. The utility of this method is demonstrated herein in assays of cytochrome P450 activity and monitoring a Suzuki-Myaura coupling reaction.

Materials/Methods

Reagents. All reagents were obtained from Sigma-Aldrich, unless otherwise noted. Disulfides used to form self-assembled monolayers were purchased from ProChimia Surfaces (Sopot, Poland). The P450 CYP2C9*1 enzyme was purchased from Corning, (Tewksbury, MA). Deionized (DI) water was prepared by a Millipore filtration unit and used for all experiments.

Figure 7:
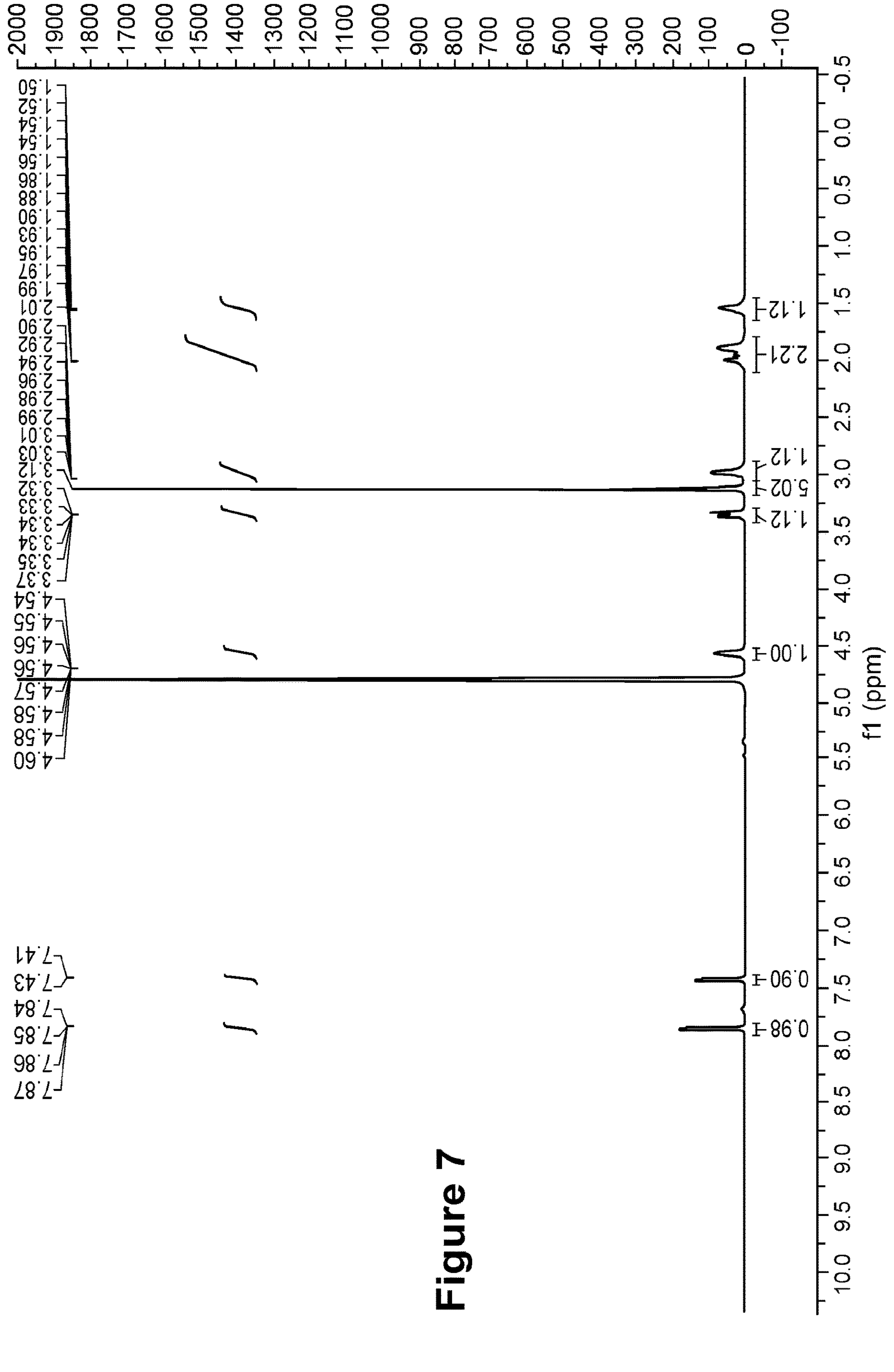
FIG. 7 shows the $^{1}$H-NMR spectrum of the photoaffinity linker.
Figure 8:
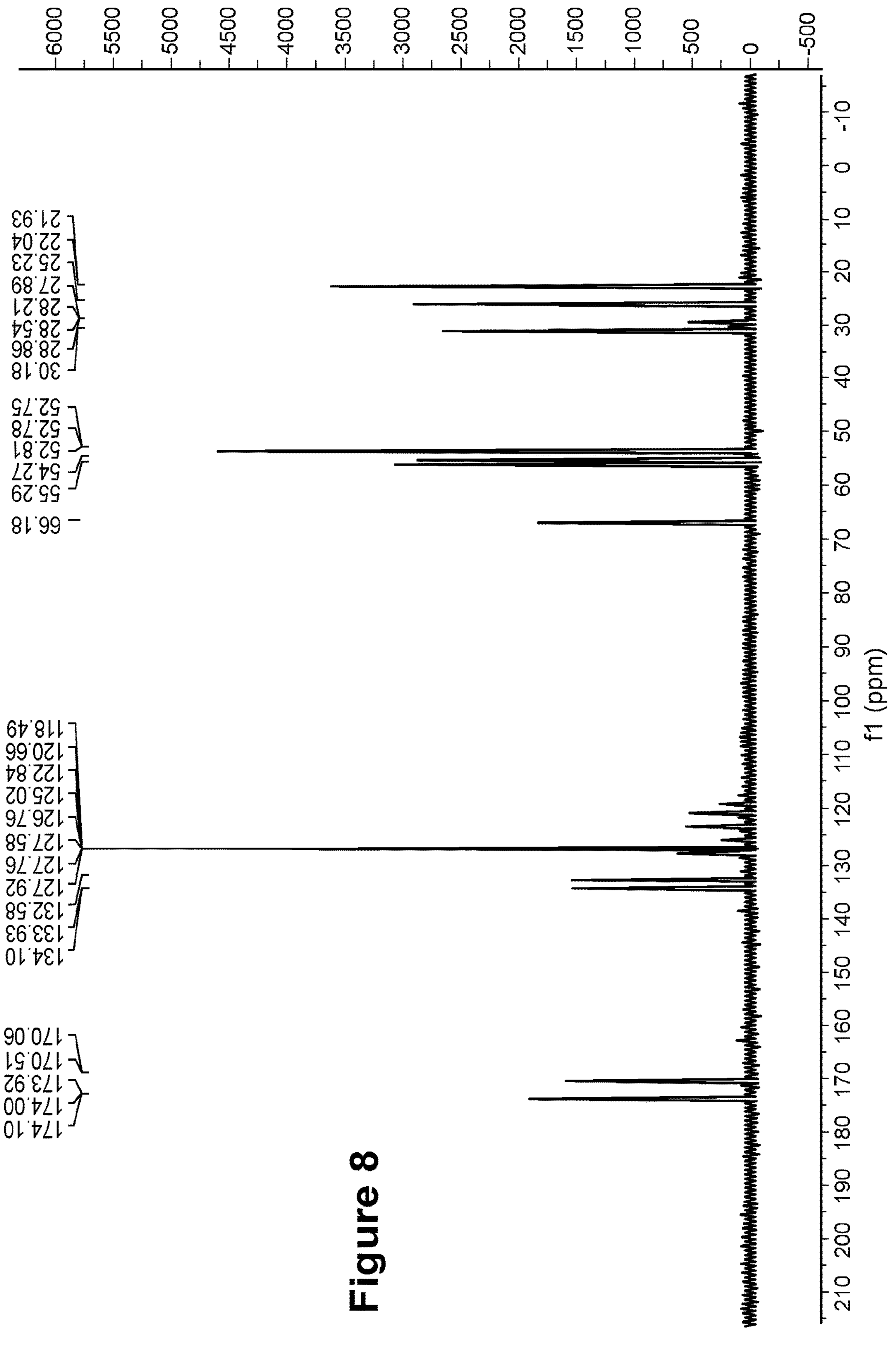
FIG. 8 shows the $^{13}$C-NMR spectrum of the photoaffinity linker.

Solid Phase Peptide Synthesis of Photo-linkers. Peptide synthesis was performed according to standard protocols. MBHA-FMOC-Rink Amide Resin was placed in a column with filters plugged. The FMOC was deprotected with 20% piperidine in dimethylformamide (DMF) for 20 minutes; the solvent was filtered with a vacuum manifold. The resin was then washed 5 times with DMF. A solution contained 4:4:8 parts of amino acid, benzotriazol-1-yl-oxytripyrrolidino-phosphonium hexafluorophosphate (PyBOP), and N-methyl morpholine was prepared and applied to the resin for 30 minutes. The solutions were then filtered; the resin was washed five times with DMF, and then the process was repeated. After the last step of the coupling, a cleavage cocktail was applied to the resin containing 95% trifluoroacetic acid (TFA), 2.5% H2O, and 2.5% triethylsilane (TES), and the resin was incubated for 2 hours. The solution was filtered with cotton to remove the resin and the remaining solution was evaporated under a stream of nitrogen. The residues were purified with liquid extraction with diethyl ether, dried with nitrogen, and lyophilized overnight. The first coupling step was for a FMOC-cysteine (Trt), the second for FMOC-Lys(Me)3-OH chloride, and the last for the photo-crosslinker group with a carboxylic acid. The diazirine group used was 4-[3-(trifluoromethyl)-3H-diaziren-3-yl]benzoic acid (TDBA), the benzophenone group used was (RS)-2-(3-benzoylphenyl)-propionic acid, and the aryl azide group used was 4-azidobenzoic acid. $^{1}H$ and $^{13}C$ NMR spectra were recorded on a Bruker Avance III 500 spectrometer. See FIGS. 7 and 8.

Preparation of Array Plates. Stainless steel plates (18×18 mm) were washed in hexanes, ethanol, deionized (DI) water, ethanol again, and then dried under nitrogen. The plates were modified by evaporation of 5 nm of titanium at a rate of 0.02 nm sec-1 (Electron Beam, Thermionics Laboratory Inc. Hayward, CA) at a pressure of $1\text{-}5\times10^{-6}$ mTorr through an aluminum mask with holes in the geometry of a standard 384-well array with 2.8 mm circles. A layer of 35 nm of gold was then deposited at 0.05 nm $sec^{-1}$. The plates were stored under vacuum until use.

Monolayer formation. The gold-coated plates were immersed in an ethanolic solution of two alkyl-disulfides (0.2 mM) where one end was functionalized with a maleimide group and the other with a tri (ethylene glycol) group in a 1:5 ratio for 16 hours at room temperature. The chips were then washed with ethanol, DI water, ethanol again, and then dried under a stream of nitrogen. A solution of the photoaffinity linker (100 μM in 100 mM Tris Buffer, pH 7.5) was applied to the plates for 30 minutes at 37° C. to immobilize the TPD group to the monolayer array.

PhotoImmobilization of Molecules. Small volumes of solutions of molecules or reaction mixtures (1 μL) were transferred onto the plates having an array of monolayers presenting the TPD group. The solutions were dried over air or in a vacuum dessicator. The plates were placed under a UV lamp sealed with nitrogen gas for 10 minutes at 1 J/cm-2. The UV lamp used was the UVP Cross-linker 1000L with 365 nm tubes. After irradiation, the plates were rinsed with ethanol, DI water, and ethanol again. Then the MALDI-matrix, 10 mg/mL solution of 2,4,6-trihydroxyacetophenone in acetone, was applied to the monolayer for analysis with the AB Sciex 5800 MALDI-TOF/TOF mass spectrometer in the reflector positive mode.

Enzyme Reactions. Reactions of CYP2C9-mediated oxidation of tolbutamide were performed in 15-μL reaction mixtures containing tolbutamide (25-1250 μM), 100 mM Tris buffer, pH 7.5, P450 CYP2C9*1 (0.4 μM) and the NADPH-regenerating system (1.3 mM NADP+, 3.3 mM glucose-6-phosphate, 3.3 mM magnesium chloride, and 0.4 U/mL glucose-6-phosphate dehydrogenase). Mixtures were preincubated at 37° C. for 5 minutes and the reactions were initiated by the addition of an NADPH-regenerating system and incubated at 37° C. Reactions were terminated at various time points (0, 30, 60 minutes) by the addition of HCl (3M, 5 μL). Proteins were removed by pelleting with high-speed centrifugation at 10,000 g for 5 minutes. The supernatants were extracted for tolbutamide and hydroxy-tolbutamide with diethyl ether. The extracted organic layer was reduced to a residue that was reconstituted in acetonitrile:water for analysis with TI-SAMDI.

Chemical Reactions. The Suzuki-Miyaura coupling reaction was performed by combining 2-bromobenzonitrile (125 mM, final concentration), potassium (4-methyl-phenyl) trifluoroborate (150 mM), and K2CO3 (125 mM) in 4 mL of ethanol:water (1:1, v/v). The catalyst, Pd(OAc)2 (1 mol %), was added to initiate the reaction. During the course of the reaction, samples (100 μL) were removed at various time points and quenched with addition of formic acid (10 μL). The catalyst was removed by filtration with cotton and diatomite, and the reaction mixtures were stored at −20° C. until analysis. A standard molecule, 4'-Methyl-2-biphenylcarboxylic acid (125 mM), having a similar structure to the product was added in equal volumes to the quenched sample. The sample was then ready for TI-SAMDI analysis.

Example 1

The strategy exemplified herein used monolayers that were functionalized with 3-trifluoromethyl-3-phenyl-diazirine (TPD). Upon irradiation with light near 365 nm, the diazirine liberates molecular nitrogen to generate a highly reactive carbene which then reacts non-selectively with a wide variety of molecules by insertion into various chemical bonds (C($sp^3$)-H, C($sp^2$)-H, O—H, C—Cl, N—H, Si—H, and C═C double bonds) to give covalent immobilization. 17-19 Hence, this photo-capture of analytes does not require that the analyte contain a specific functional group for immobilization and therefore can be broadly applicable in characterizing reaction products. The photoaffinity linker was synthesized using standard routes[15] to couple a 4-[3-(trifluoromethyl)-3H-diazirin-3-yl]benzoic acid with trimethyl ammonium lysine and cysteine. The trimethylated lysine was included because it enhances the MALDI ionization efficiency[20] and the cysteine residue was included for immobilization to self-assembled monolayers presenting maleimide groups.[21]

First, monolayers presenting a maleimide group was prepared at a density of 20% against a background of tri (ethylene glycol) groups on gold-coated metal chips as described previously.[22]

A solution of the photoaffinity linker (100 μM in 100 mM Tris Buffer, pH 7.5) was applied for 30 minutes at 37° C. to immobilize the TPD group. It was found that the photoimmobilization reactions were most efficient when the solvent was first evaporated with a vacuum desiccator to leave a dried film on the monolayer prior to irradiation at 365 nm with a UV lamp for 10 min at 1 $J/cm^2$ under a nitrogen atmosphere. Drying the molecules onto the surface increased their concentration and minimizes immobilization of solvent molecules[17] whereas the nitrogen gas minimized oxidation of the SAMs.[23] After irradiation, the monolayer was rinsed and treated with 2,4,6-trihydroxyacetophenone (THAP) composition (10 mg/mL in acetone) and analyzed by MALDI mass spectrometry. The resulting spectra revealed mass shifts that correspond to the covalent addition of the small molecule to the TPD terminated alkanethiolate after loss of nitrogen.

Figure 2:
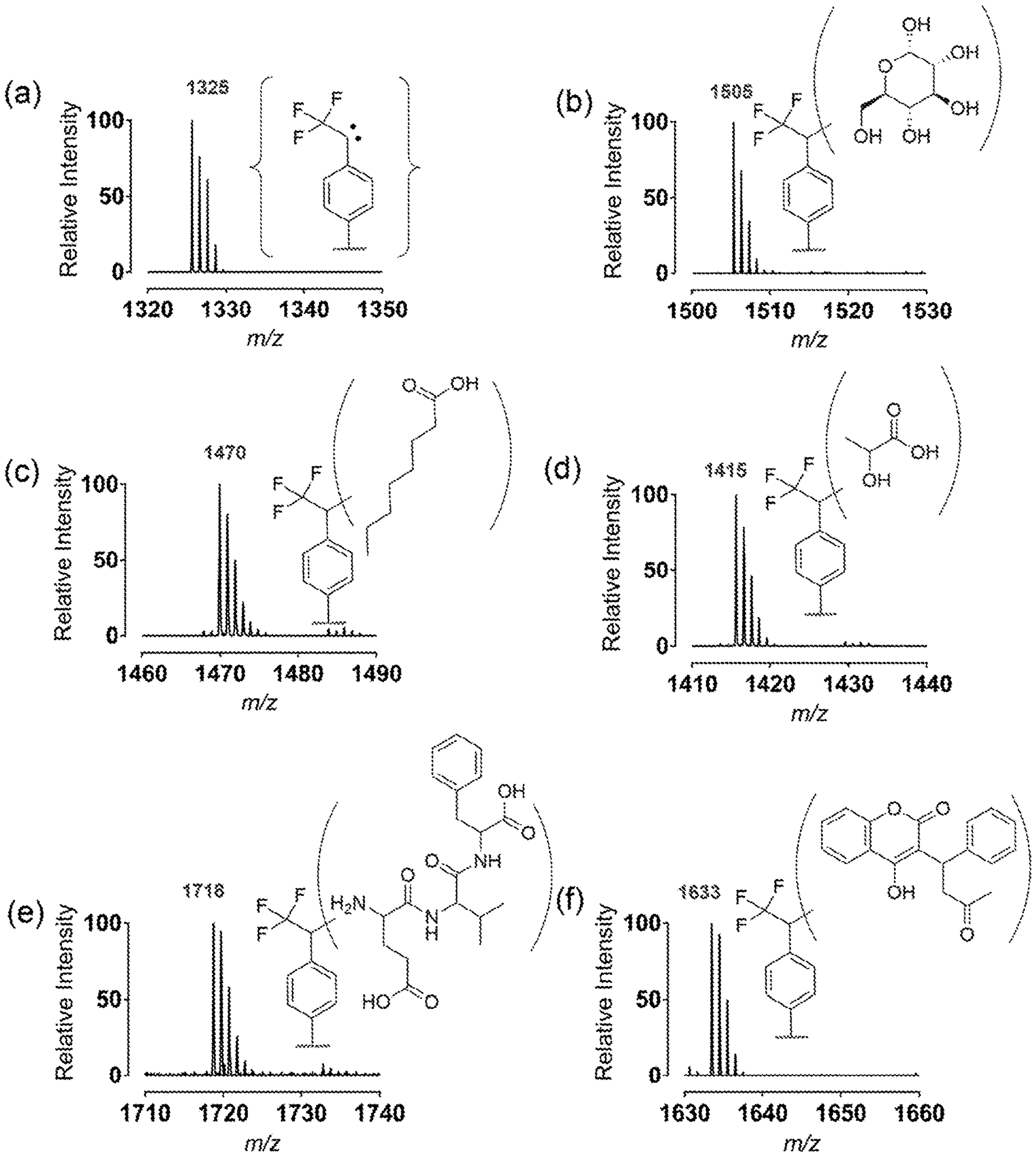
FIG. 2 shows examples of SAMDI spectra for the photoimmobilization of several molecules. (a) the initial monolayer presenting TFD groups; (b) the carbohydrate glucose; (c) the lipid caprylic acid; (d) the metabolite lactic acid; (e) the tripeptide Glu-Val-Phe; (f) and the drug warfarin. The products depict that the molecules immobilize by nonspecific reaction of the carbene with multiple bonds in the molecules, giving a mixture of isomeric products.
Figure 4:
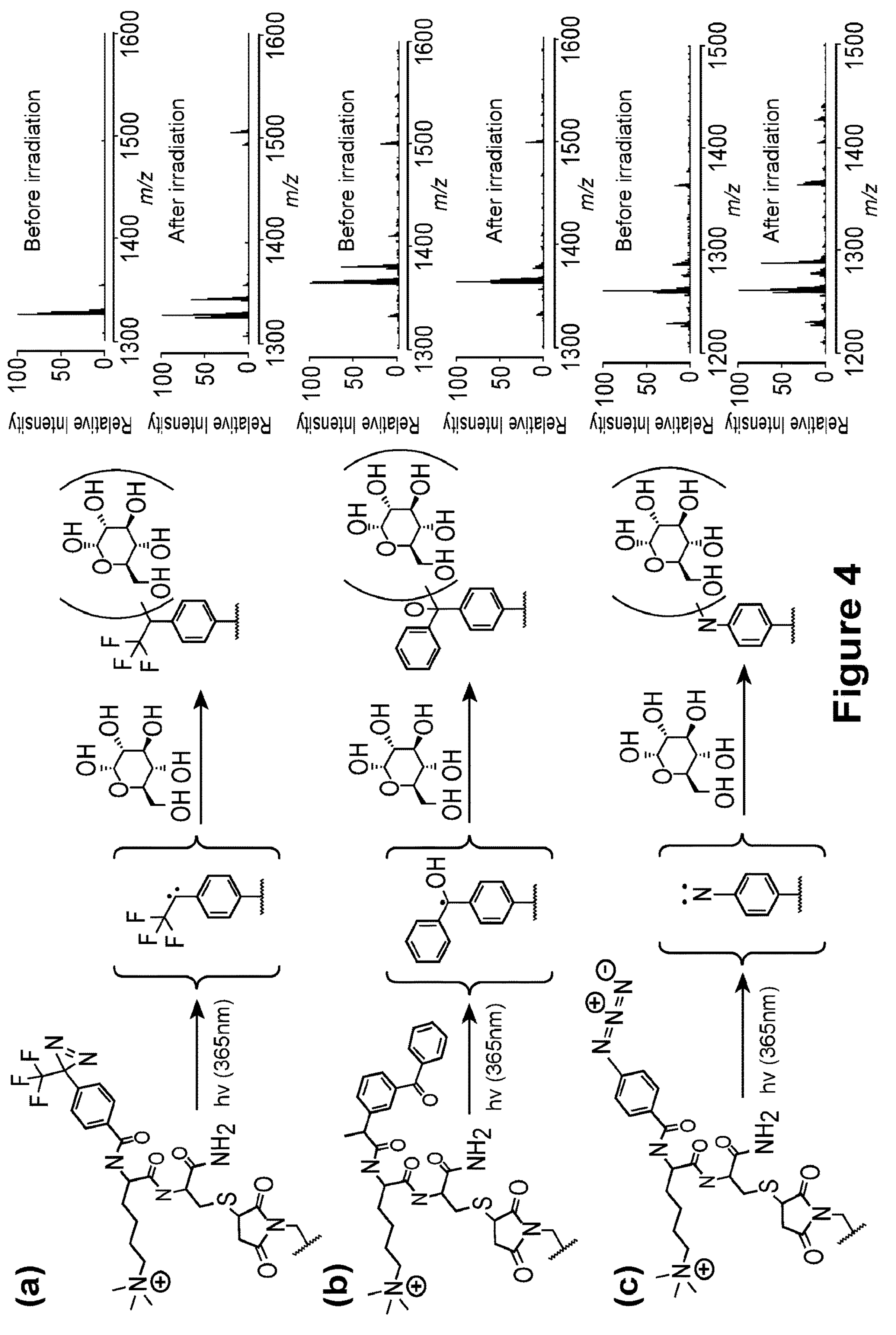
FIG. 4 depicts a comparison of three photoimmobilization strategies for glucose. Spectra are shown for monolayers presenting each of the three photoactive groups; (a) diazirine; (b) benzophenone; (c) arylo azide, before and after irradiation to immobilize glucose. (a) The diazirine-terminated alkanethiol appears at m/z 1325 (after loss of nitrogen and conversion to carbene during the MALDI experiment) and showed the expected peak after immobilization of glucose (m/z 1505) The byproducts are due to reaction with water (m/z 1341) and 2,4,6-trihydroxyacetophenone (m/z 1493), the MALDI matrix. (b) The benzophenone group (m/z 1363) showed no reaction with glucose after irradiation, (c) and the aryl azide group (m/z 1261) showed inefficient immobilization of glucose with many byproducts.

A SAMDI spectrum presenting the TPD group in a mixed monolayer that included the tri (ethylene glycol)-terminated alkanethiolate was first obtained. The spectrum (FIG. 2*a*) showed a peak at m/z 1325 corresponding to the mixed disulfide wherein the diazirine expelled nitrogen, presumably during the laser irradiation. Traceless immobilization of several molecules and analysis by SAMDI was then demonstrated. First, a solution of glucose (1 mM in 1 L of water) was applied to the monolayer and obtained a spectrum as described above. The spectrum (FIG. 2*b*) showed a peak (m/z 1505) corresponding to a mass shift consistent with the addition of glucose. Likewise, the immobilization of several other molecules was performed to demonstrate the generality of the technique, including caprylic acid (1 mM in water), lactic acid (1 mM in water), the tri-peptide Glu-Val-Phe (1 mM in water) and the drug warfarin (1 mM in water). SAMDI spectra of the photo-immobilized molecules revealed clean peaks at m/z 1470 (FIG. 2*c*), m/z 1415 (FIG. 2*d*), m/z 1718 (FIG. 2*e*), and m/z 1633 (FIG. 2*f*) respectively. These examples demonstrated that the TI-SAMDI-MS method covalently captured a broad range of molecular structure types and that could be analyzed with SAMDI mass spectrometry. It was noted that monolayers were first evaluated presenting either an aryl azide or a benzophenone group and in both cases insufficient reaction was observed with small molecules compared to the diazirine presenting monolayers (FIG. 4).

Example 2

The importance of traceless immobilization of analytes is evident in assays of drug metabolizing enzymes. It is necessary to characterize the activities of various P450 isoforms on FDA-approved drugs to identify drug-drug interactions and to determine appropriate doses. The use of an analogue of a drug that is modified to include an immobilization tag carries the risk that the functional group will alter the activity towards a metabolizing enzyme.[16] To demonstrate this application, hydroxylation of the drug tolbutamide by CYP2C9*1, a P450 liver enzyme, was assayed.[16] The enzyme (0.4 μM), and tolbutamide (50 μM) were combined in 15 μL of Tris buffer (100 mM, pH 7.5) with the NADPH-regenerating system (1.3 mM NADP+, 3.3 mM glucose-6-phosphate, 3.3 mM magnesium chloride, and 0.4 U/mL glucose-6-phosphate dehydrogenase) and allowed to react for 0 and 60 minutes at 37° C. HCl (3 M, 5 L) was then added to quench the reactions, and proteins were removed by centrifugation, followed by extraction of tolbutamide and hydroxytolbutamide with diethyl ether. The extracted organic layer was reduced to a residue that was reconstituted in acetonitrile:water (1:1, v/v). The purified samples were then spotted onto the monolayers as described above and analyzed by TI-SAMDI MS showing the photo-immobilized peak for tolbutamide (m/z 1595) and for the hydroxy-tolbutamide (m/z 1611, FIG. 3*a*). This example demonstrated that the TI-SAMDI-MS method can be used in monitoring reactions.

Figure 3:
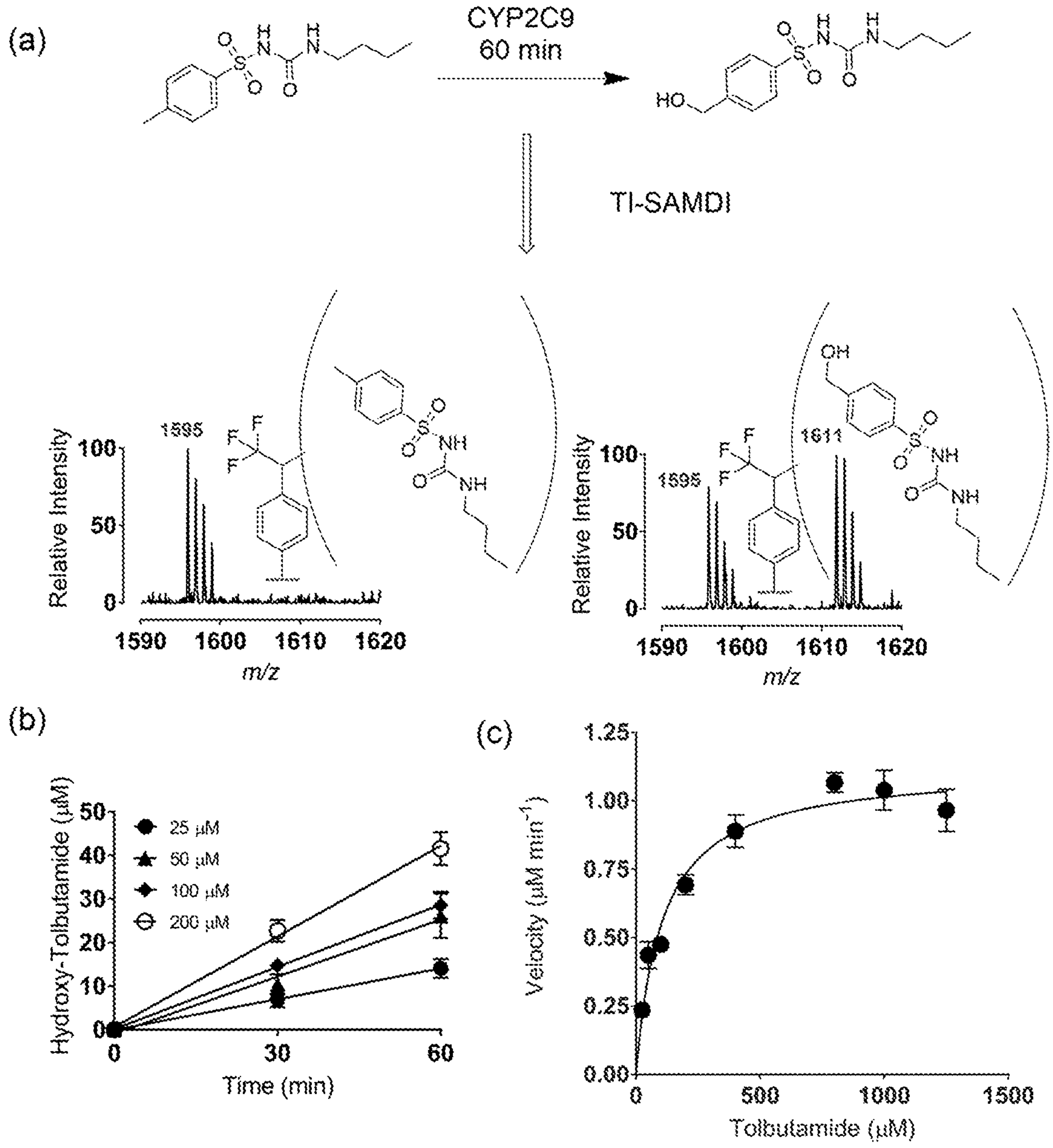
FIG. 3 depicts a quantitative application of TI-SAMDI-MS. (a) Spectra showing before and after CYP2C9 enzyme reaction of tolbutamide to hydroxy-tolbutamide by hydroxylation. (b) Plot showing product yield concentration of hydroxy-tolbutamide to reaction times for calculation of velocity for enzyme kinetics. (c) Michaelis-Menten kinetic plot of reaction as determined by TI-SAMDI-MS.
Figure 5:
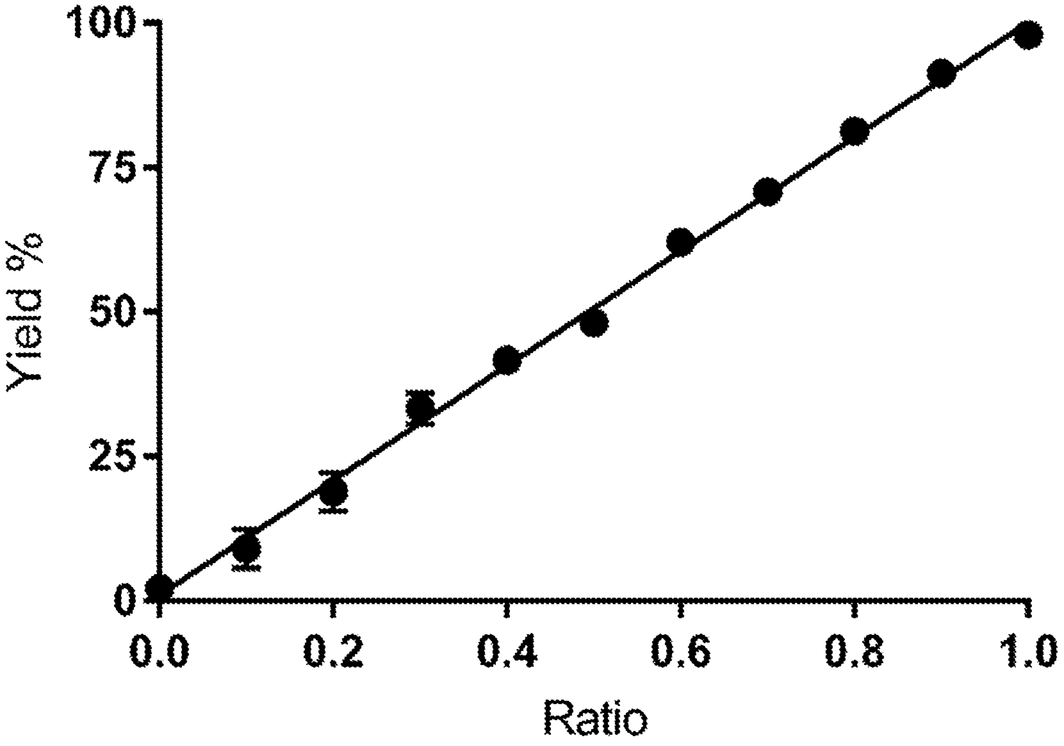
FIG. 5 shows a calibration curve for tolbutamide and hydroxy-tolbutamide. A series of solutions having a range of hydroxytolbutamide to tolbutamide ratios, at a constant total concentration were prepared, photoimmobilized as described herein, and analyzed by SAMDI MS. The measured fractions of hydroxy-tolbutamide (determined from the peak intensity for hydroxy-tolbutamide divided by the sum of the intensities for hydroxy-tolbutamide and tolbutamide) were linearly related to the actual fractions, demonstrating that these molecules had similar ionization efficiencies.

The kinetics for this reaction were then characterized. A series of reactions were performed for tolbutamide concentrations ranging from 25 μM to 1.25 mM and reaction times of 0 minutes, 30 minutes and 60 minutes. The reactions were quenched and processed as described above to obtain SAMDI spectra. The yield of the enzymatic conversion was calculated by finding the ratio of the peak integration for hydroxy-tolbutamide relative to the sum of the peak areas for hydroxy-tolbutamide ($A_{HTolb}$) and tolbutamide ($A_{Tolb}$) (percentage yield=$A_{HTolb}$/[$A_{HTolb}$+$A_{Tolb}$]×100). These data were fit with a straight line to obtain the initial rates for the reactions, which increased smoothly with increasing tolbutamide concentration and reached a maximum as shown in the Michaelis-Menten plot (FIG. 3*c*). $K_M$ and $K_{cat}$ were calculated to be 106 μM (95% CI: 59.3 to 153 μM) and 2.8 min 1 (2.5 to 3.1 $min^{-1}$), respectively. Previous studies found 78 μM (95% CI: 34.2 to 122 μM) and 2.31 $min^{-1}$ (2.45 to 3.44 $min^{-1}$) as done by high-performance liquid chromatography (HPLC).[16] It was noted that when quantitating yields from the mass spectra it is important to recognize that the substrate and product may have different ionization efficiencies and that the yields may be skewed. To address this possibility, a calibration was performed, where defined mixtures of the substrate and product were photo-immobilized and then quantitated by SAMDI MS. It was found that the measured fraction of product was linearly related to the actual values, showing that these molecules had similar ionization efficiencies (FIG. 5). These results demonstrated that TI-SAMDI MS can quantitatively characterize enzyme reactions similarly to HPLC enzyme characterization, but in a format more amenable to high-throughput characterization of enzymes.

Example 3

Figure 6:
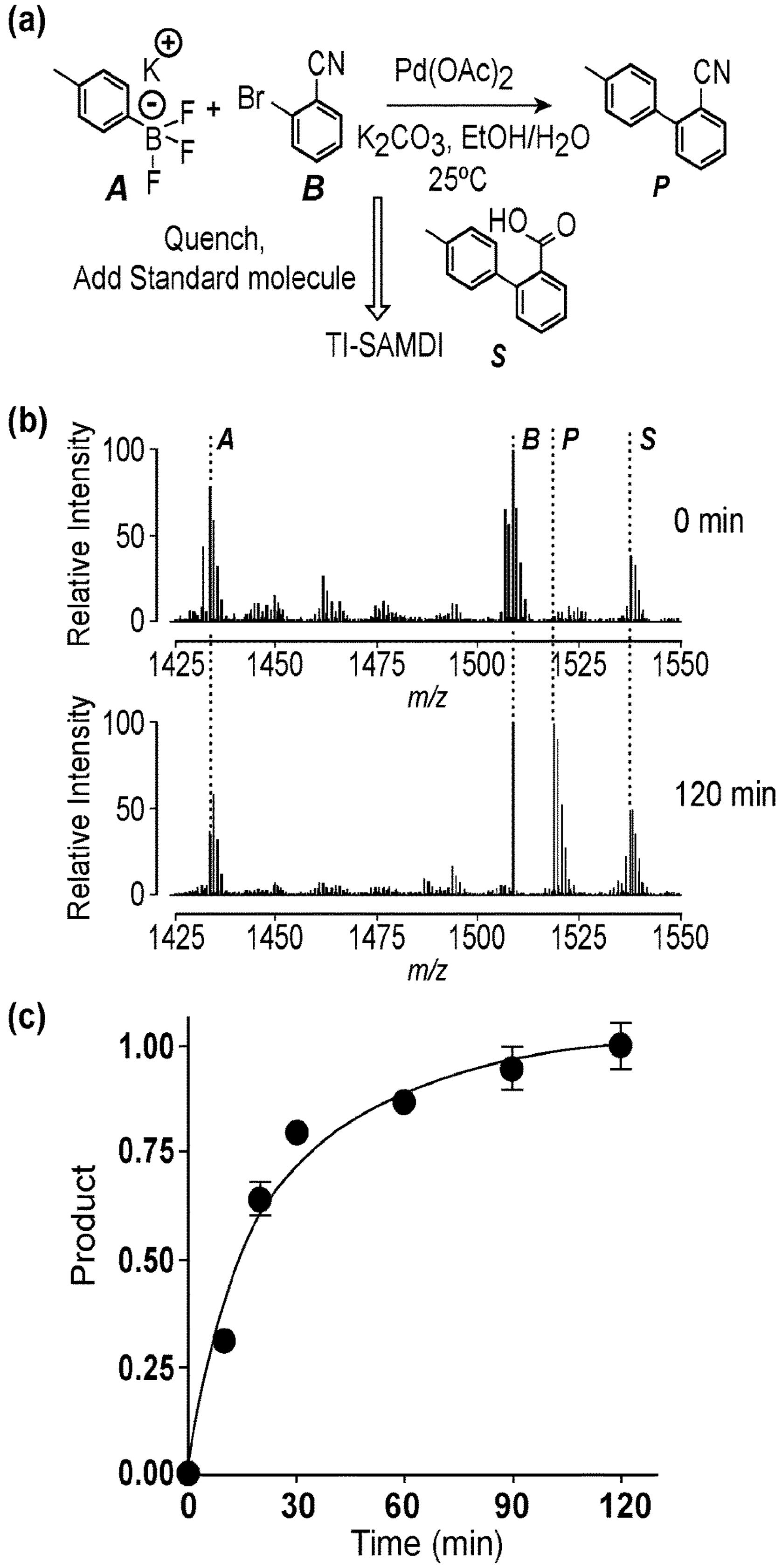
FIG. 6 shows results of experiments in which TI-SAMDI was used to analyze a Suzuki-Myaura coupling reaction between potassium (4-methyl-phenyl)trifluoroborate [A] and 2-bromobenzonitrile [B] to give the biphenyl product [P]. A standard [S] molecule was added to the quenched reactions to permit quantitation of the product. (c) TI-SAMDI spectra at 0 min and 120 min. (d) The ratio of product to the standard was used to determine the yield at several reaction times.

It was next demonstrated that TI-SAMDI can be used to characterize chemical reactions. The Suzuki-Miyaura coupling of 2-bromobenzonitrile (125 mM) and potassium 4-methylphenyltrifluoroborate (150 mM), with a $Pd(OAc)_2$ catalyst (1 mol %) in ethanol/water (4 mL) to give 4'-methyl-2-biphenylcarbonitrile[26] was repeated (FIG. 6*a*). The reaction was performed at 25° C. for 120 minutes, but with removal of small volumes (100 μL) at select time intervals that were terminated with formic acid (10 μL), filtered with cotton and diatomite to remove the palladium catalyst.

A standard molecule, 4'-methyl-2-biphenylcarboxylic acid, was added to each sample at a known concentration (125 mM) and served as a calibrant to permit quantitation of product yields. The samples were photoimmobilized as described earlier and analyzed with TI-SAMDI (FIG. 6*b*). The potassium (4-methyl-phenyl)trifluoroborate degrades to 4-methylphenol and is visible in a peak at m/z 1433 at 0 minutes and 120 minutes. The 2-bromobenzonitrile appears at m/z 1507 and is absent after two hours of reaction. The product appears at m/z 1518 and the standard appears at m/z 1537. Yields were determined from the ratio of product to the standard to give a kinetic profile for the reaction (FIG. 6*c*). This example illustrated the utility of TI-SAMDI to rapidly monitor organic chemical reactions in solution.

Conclusions

The examples demonstrated label-free approach for high-throughput reactions. The ability to photo-immobilize any analyte to a self-assembled monolayer allows the use of SAMDI mass spectrometry to quantitate the conversion of an analyte to a product and is well-suited to perform thousands of experiments per day. This method is also relevant in studies where analytes are either unknown or cannot be modified with functional groups for subsequent immobilization, as is the case with the cytochrome P450 enzyme demonstrated herein. In some embodiments, the TI-SAMDI method requires that the relevant analytes be present at a sufficient molecular fraction (greater than approximately 10%) and that their masses not overlap with those of other components in the reaction mixture.

Another benefit of the TI-SAMDI-MS method is that it removes the difficulty of MALDI methods to detect low molecular weight compounds, since conjugation of the molecules to the alkanethiol serves to increase the mass and remove it from the matrix peaks in the spectrum. The methods of the disclosure represent a significant extension of the SAMDI assay and addresses prior concerns regarding the need to modify analytes for immobilization.

REFERENCES (1) Shevlin, M. ACS Med. Chem. Lett. 2017, 8, (6), 601-607.
(2) Selekman, J. A.; Qiu, J.; Tran, K.; Stevens, J.; Rosso, V.; Simmons, E.; Xiao, Y.; Janey, J. Annu. Rev. Chem. Biomol. Eng. 2017, 8, 525-547.
(3) Krska, S. W.; DiRocco, D. A.; Dreher, S. D.; Shevlin, M. Acc. Chem. Res. 2017, 50, (12), 2976-2985.
(4) de Rond, T.; Danielewicz, M.; Northen, T. Curr. Opin. Biotechnol. 2015, 31, 1-9.
(5) Su, J.; Mrksich, M. Angew. Chem. Int. Ed. 2002, 41, (24), 4715-8.
(6) Min, D. H.; Su, J.; Mrksich, M. Angew. Chem. Int. Ed. 2004, 43, (44), 5973-7.
(7) Min, D. H.; Tang, W. J.; Mrksich, M. Nat. Biotechnol. 2004, 22, (6), 717-23.
(8) Ban, L.; Pettit, N.; Li, L.; Stuparu, A. D.; Cai, L.; Chen, W.; Guan, W.; Han, W.; Wang, P. G.; Mrksich, M. Nat. Chem. Biol. 2012, 8, (9), 769-73.
(9) Gurard-Levin, Z. A.; Scholle, M. D.; Eisenberg, A. H.; Mrksich, M. ACS Comb. Sci. 2011, 13, (4), 347-50.
(10) Su, J.; Rajapaksha, T. W.; Peter, M. E.; Mrksich, M. Anal. Chem. 2006, 78, (14), 4945-51.
(11) Gurard-Levin, Z. A.; Kilian, K. A.; Kim, J.; Bahr, K.; Mrksich, M. ACS Chem. Biol. 2010, 5, (9), 863-73.
(12) Ban, L.; Mrksich, M. Angew. Chem. Int. Ed. 2008, 47, (18), 3396-9.
(13) Tsubery, H.; Mrksich, M. Langmuir 2008, 24, (10), 5433-8.
(14) Patrie, S. M.; Roth, M. J.; Plymire, D. A.; Maresh, E.; Zhang, J. Anal. Chem. 2013, 85, (21), 10597-604.
(15) Kuo, H. Y.; DeLuca, T. A.; Miller, W. M.; Mrksich, M. Anal. Chem. 2013, 85, (22), 10635-10642.
(16) Anderson, L. L.; Berns, E. J.; Bugga, P.; George, A. L., Jr.; Mrksich, M. Anal. Chem. 2016, 88, (17), 8604-9.
(17) Kanoh, N.; Kumashiro, S.; Simizu, S.; Kondoh, Y.; Hatakeyama, S.; Tashiro, H.; Osada, H. Angew. Chem. Int. Ed. 2003, 42, (45), 5584-7.
(18) Kanoh, N.; Kyo, M.; Inamori, K.; Ando, A.; Asami, A.; Nakao, A.; Osada, H. Anal. Chem. 2006, 78, (7), 2226-30.
(19) Kanoh, N.; Asami, A.; Kawatani, M.; Honda, K.; Kumashiro, S.; Takayama, H.; Simizu, S.; Amemiya, T.; Kondoh, Y.; Hatakeyama, S.; Tsuganezawa, K.; Utata, R.; Tanaka, A.; Yokoyama, S.; Tashiro, H.; Osada, H. Chem. Asian J. 2006, 1, (6), 789-97.
(20) Roth, K. D. W.; Huang, Z.-H.; Sadagopan, N.; Watson, J. T. Mass Spectrometry Reviews 1998, 17, (4), 255-274.
(21) Houseman, B. T.; Gawalt, E. S.; Mrksich, M. Langmuir 2003, 19, (5), 1522-1531.
(22) Yeo, W. S.; Min, D. H.; Hsieh, R. W.; Greene, G. L.; Mrksich, M. Angew Chem. Int. Ed. 2005, 44, (34), 5480-3.
(23) Huang, J.; Hemminger, J. C. J. Am. Chem. Soc. 1993, 115, (8), 3342-3343.
(24) Diagne, A. B.; Li, S.; Perkowski, G. A.; Mrksich, M; Thomson, R. J. ACS Comb. Sci. 2015. 17 (11): 658-662.
(25) Montavon, T. J., Li. J; Cabrera-Pardo, J. R.; Mrksich, M.; Koazmin, S. A. Nat. Chem. 2011, 4 (1): 45-51
(26) Liu, C.; Li, X.; Gao, Z.; Wang, X.; Jin, Z. Tetrahedron. 2015, 71, 3954-3959

What is claimed is:

1. A self-assembled monolayer-substrate composition, comprising: a self-assembled monolayer (SAM) attached to at least a portion of the substrate surface, wherein the SAM comprises an alkyl chain having a reactive group at one terminus for association with the substrate surface, a spacer group, and a traceless linker at the terminus opposite the substrate surface, wherein the traceless linker is attached to the SAM via complementary reactive groups and is capable of reacting with an analyte upon exposure to ultraviolet light.

2. The composition of claim 1, wherein the spacer comprises two to twenty ethylene glycol groups.

3. The composition of claim 1, wherein the spacer has a structure of

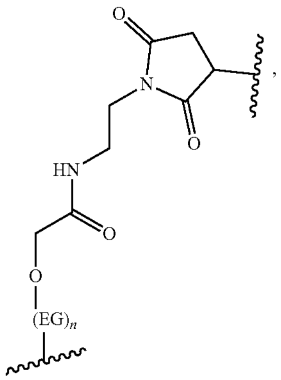

wherein EG is ethylene glycol, and n is 2-20.

4. The composition of claim 3, wherein n is 2-5.

5. The composition of claim 1, wherein the traceless linker comprises a diazirine.

6. The composition of claim 1, wherein the traceless linker comprises 3-trifluoromethyl-3-phenyl-diazirine (TPD).

7. The composition of claim 1, wherein the traceless linker forms a carbene upon exposure to ultraviolet light.

8. The composition of claim 1, wherein the density of traceless linker is from about 0.1% to 100%.

9. The composition of claim 1, wherein the density of traceless linker is from about 10% to about 50%.

10. A method of making the composition of claim 1, comprising contacting the substrate with the alkyl chain having a reactive group at one terminus to attach the alkyl chain to at least a portion of the substrate surface to form the SAM, wherein at least a portion of alkyl chains of the SAM further comprise a spacer group and/or a reactive group at the opposite terminus to attach the traceless linker, and contacting the reactive group and the traceless linker to attach the traceless linker via a complementary reactive group on the traceless linker.

11. The method of claim 10, wherein the reactive group on the traceless linker comprises a maleimide.

12. The method of claim 10, wherein the reactive group on the alkyl chain or the reactive group on the traceless linker comprises an azide, an alkyne, a maleimide, a thiol, an alcohol, an amine, a carboxylic acid, an olefin, an isothiocyanate, a N-hydroxysuccinimide, a phosphine, a nitrone, a norbornene, an oxanorbornene, a transcycloctene, an s-tetrazene, an isocyanide, a tetrazole, a nitrile oxide, a quadricyclane, or a carbodiimide to react with the maleimide.

13. The method of claim 12, further comprising contacting the composition and an analyte under ultraviolet light to attach the analyte.

14. The method of claim 13, wherein the analyte comprises a protein, a peptide, an antibody, an oligonucleotide, a small molecule, a carbohydrate, a metabolite, an amino acid, a fatty acid, a lipid, a drug, or a reaction product.

15. A method of measuring activity of an enzyme, comprising (a) contacting the enzyme with an enzyme analyte to form a reaction mixture; wherein the enzyme analyte, upon contact with the enzyme, forms a product, such that the enzyme analyte and the product comprise different masses;

(b) contacting the reaction mixture of (a) with the composition of claim 1 such that the enzyme analyte and the product are attached to the composition via reaction with the traceless linker in the presence of ultraviolet light;

(c) subjecting the composition to mass spectrometry to produce a mass spectrum having an enzyme analyte signal and an product signal; and (d) measuring the activity of the enzyme by correlating a signal intensity of the enzyme analyte signal to a signal intensity of the product signal to determine the extent of product formation and thereby measuring the activity of the enzyme.

16. The method of claim 15, wherein the enzyme is a deacetylase, acetyltransferase, esterase, phosphorylase/kinase, phosphatase, protease, methylase, demethylase, or a DNA or RNA modifying enzyme.

17. A method of monitoring a chemical reaction, comprising (a) contacting two or more reactants of the chemical reaction to form a reaction mixture; wherein the two or more reactants, upon contact, forms a product, such that the reactants and the product comprise different masses;

(b) contacting the reaction mixture of (a) with the composition of claim 1 such that the reactant and the product are attached to the composition via reaction with the traceless linker in the presence of ultraviolet light;

(c) subjecting the composition to mass spectrometry to produce a mass spectrum having a product signal and reactant signals, one for each reactant; and (d) monitoring the chemical reaction by correlating a signal intensity of at least one of the reactant signals to a signal intensity of the product signal to determine the extent of product formation and thereby monitoring the chemical reaction.

18. The method of claim 17, wherein the chemical reaction is a Suzuki reaction, and the two or more reactants comprise an organoboron and a halide compound.

* * * * *